(12) United States Patent
Ito et al.

(10) Patent No.: US 9,481,871 B2
(45) Date of Patent: Nov. 1, 2016

(54) NUCLEIC ACID ENCODING A POLPEPTIDE HAVING AMINOTRANSFERASE ACTIVITY, VECTORS AND HOST CELLS COMPRISING THE NUCLEIC ACID

(75) Inventors: Noriyuki Ito, Takasago (JP); Akiko Nishi, Takasago (JP); Shigeru Kawano, Takasago (JP); Yoshihiko Yasohara, Takasago (JP)

(73) Assignee: KANEKA CORPORATION, Osaka (JP)

( * ) Notice: Subject to any disclaimer, the term of this patent is extended or adjusted under 35 U.S.C. 154(b) by 66 days.

(21) Appl. No.: 13/876,412

(22) PCT Filed: Sep. 28, 2011

(86) PCT No.: PCT/JP2011/072237
§ 371 (c)(1),
(2), (4) Date: Mar. 27, 2013

(87) PCT Pub. No.: WO2012/043653
PCT Pub. Date: Apr. 5, 2012

(65) Prior Publication Data
US 2013/0196389 A1 Aug. 1, 2013

(30) Foreign Application Priority Data
Sep. 28, 2010 (JP) .................. 2010-216546

(51) Int. Cl.
C07H 21/00 (2006.01)
C12N 1/15 (2006.01)
C12N 1/19 (2006.01)
C12N 1/21 (2006.01)
C12N 9/10 (2006.01)
C12P 41/00 (2006.01)
C12P 17/10 (2006.01)

(52) U.S. Cl.
CPC ............ *C12N 9/1096* (2013.01); *C12P 17/10* (2013.01); *C12P 41/006* (2013.01); *C12Y 206/01* (2013.01); *Y02P 20/52* (2015.11)

(58) Field of Classification Search
CPC . C12N 9/1096; C12Y 206/01; C12P 41/006; C12P 17/10
See application file for complete search history.

(56) References Cited

U.S. PATENT DOCUMENTS

2010/0285544 A1 11/2010 Ito et al.

FOREIGN PATENT DOCUMENTS

JP 2007-185133 A 7/2007
WO WO-2006126498 A1 11/2006

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Yamamoto et al., GenBank accession No. DJ063479, Jan. 23, 2008.*
Ausubel, F., Current Protocols in Molecular Biology, Hybridization Analysis of DNA Blots, pp. 2.10.8-2.10.11.*
Guo et al., PNAS 101(25):9205-9210, 2004.*
Koszelewski et al., "(ω-Transaminases for the synthesis of non-racemic α-chiral primary amines", Trends in Biotechnology, 2010-06, vol. 28, No. 6, pp. 324-332.
Hohne et al., "A Protection Strategy Substantially Enhances Rate and Enantioselectivity in ω-transaminase-Catalyzed Kinetic Resolutions", Adv. Synth. Catal., 2008, vol. 350, pp. 807-812.

* cited by examiner

*Primary Examiner* — Delia Ramirez
(74) *Attorney, Agent, or Firm* — Polsinelli PC

(57) ABSTRACT

A method for inexpensively and efficiently producing an optically active amino compound useful as an intermediate for pharmaceutical preparations, agricultural chemicals, or the like, from a ketone compound is provided. Specifically, a polypeptide exhibiting higher activity for glutamic acid as an amino donor than that for L-alanine, and, having novel transaminase activity for generating (S)-1-benzyl-3-pyrrolidinone with high optical purity of 93% or more, a gene encoding the same, and a transformant expressing the gene at a high level are also provided herein.

3 Claims, No Drawings

NUCLEIC ACID ENCODING A POLPEPTIDE HAVING AMINOTRANSFERASE ACTIVITY, VECTORS AND HOST CELLS COMPRISING THE NUCLEIC ACID

CROSS REFERENCE TO RELATED APPLICATIONS

This application is a National Phase filing under 35 U.S.C. §371 of PCT/JP2011/072237 filed on Sep. 28, 2011; and this application claims priority to Application No. 2010-216546 filed in Japan on Sep. 28, 2010, under 35 U.S.C. §119; the entire contents of all are hereby incorporated by reference.

TECHNICAL FIELD

The present invention relates to an enzyme capable of efficiently converting a ketone compound to an optically active amino compound through transamination and a method for producing an optically active amino compound using the enzyme. The thus obtained optically active amino compound can be used as an intermediate for pharmaceutical preparations, agricultural chemicals, or the like.

BACKGROUND ART

Regarding methods for producing optically active amines using transaminases, there are many reports concerning methods for producing α-amino acid, but there are few reports concerning methods for producing optically active amine compounds other than α-amino acid. In recent years, a transaminase that generates optically active amines other than α-amino acid has been discovered, and the use thereof for a general method for efficiently producing optically active amines is expected.

However, transaminases known to date for generation of optically active amines other than α-amino acid have had many problems (Non-patent Document 1).

For example, it is useful to enzymatically remove α-keto acid generated as a by-product by using α-amino acid as an amino group donor. However, α-amino acid that acts as an amino group donor is substantially limited to alanine, which is expensive and has low solubility.

Among optically active amino compounds other than α-amino acid, a transaminase that generates (S)-1-benzyl-3-aminopyrrolidine, that is, a particularly useful pharmaceutical intermediate with high optical purity of 93% e.e. or more, has remained undiscovered (Patent Documents 1 and 2 and Non-patent Document 2).

PRIOR ART DOCUMENTS

Patent Documents

Patent Document 1: JP Patent Publication (Kokai) No. 2007-185133 A
Patent Document 2: WO2006/126498

Non-Patent Documents

Non-patent Document 1: Trends in Biotechnology 28, 324-332 (2010)

Non-patent Document 2: Adv. Synth. Catal. 350, 807-812 (2008)

SUMMARY OF THE INVENTION

Problems to be Solved by the Invention

An object of the present invention is to provide a method for efficiently producing optically active amino compounds useful as intermediates for pharmaceutical preparations, agricultural chemicals, and the like, from ketone compounds.

Means for Solving the Problem

As a result of screening for various soil isolates, the present inventors have discovered a microorganism having catalytic activity for transamination, generating (S)-1-benzyl-3-aminopyrrolidine with high optical purity of 93% e.e. or more, and exhibiting high activity for glutamic acid as an amino group donor that is inexpensive and has high solubility. They have further succeeded in isolation and purification of a polypeptide having the activity from the microorganism. Furthermore, they have obtained a gene encoding the polypeptide by gene recombination techniques, and have revealed the nucleotide sequence thereof. Moreover, they have established a method that involves breeding a transformant producing the enzyme with the use of the gene, and then preparing a highly active transformant, so as to allow industrial production of optically active amino compounds.

Specifically, the present invention relates to a polypeptide having the following physico-chemical properties (1) to (6).
(1) Function: It catalyzes transamination by acting on 1-benzyl-3-pyrrolidinone in the presence of an amino group donor to generate (S)-1-benzyl-3-aminopyrrolidine with optical purity of 93% e.e. or more.
(2) Substrate specificity:
(a) Amino group donor: It exhibits activity for (S)-1-phenethylamine, exhibits higher activity for L-glutamic acid than that for L-alanine, and does not substantially exhibit activity for β-alanine and 4-aminobutyric acid.
(b) Amino group receptor: It exhibits higher activity for 2-ketoglutaric acid than that for pyruvic acid.
(3) Optimum pH: 7.0 to 8.0
(4) Optimum temperature: 30° C. to 50° C.
(5) Thermal stability: It retains residual activity equivalent to 70% or more of total activity before treatment when treated at pH 8.0 and 30° C. to 50° C. for 30 minutes.
(6) Molecular weight: about 48 kDa as measured by sodium dodecyl sulfate-polyacrylamide gel electrophoresis.

The present invention further relates to a polypeptide consisting of an amino acid sequence that has 50% or more sequence identity with the amino acid sequence shown in SEQ ID NO: 1 in the sequence listing, and having activity to act on 1-benzyl-3-pyrrolidinone in the presence of an amino group donor to generate (S)-1-benzyl-3-aminopyrrolidine with optical purity of 93% e.e. or more.

The present invention further relates to a polypeptide consisting of an amino acid sequence that has 50% or more sequence identity with the amino acid sequence shown in SEQ ID NO: 1 in the sequence listing, and exhibiting activity for (S)-1-phenethylamine, exhibiting higher activity for L-glutamic acid than that for L-alanine, and not substantially exhibiting activity for β-alanine and 4-aminobutyric acid as an amino group donor, and exhibiting higher activity for 2-ketoglutaric acid than that for pyruvic acid as an amino group receptor.

The present invention further relates to a polypeptide having an amino acid sequence that has a deletion, a substitution, an insertion, or an addition of 1 or more amino acids with respect to the amino acid sequence shown in SEQ ID NO: 1 in the sequence listing, and having activity to act on 1-benzyl-3-pyrrolidinone in the presence of an amino group donor to generate (S)-1-benzyl-3-aminopyrrolidine with optical purity of 93% e.e. or more.

Alternatively, the present invention relates to a polypeptide having an amino acid sequence that has a deletion, a substitution, an insertion, or an addition of 1 or more amino acids with respect to the amino acid sequence shown in SEQ ID NO: 1 in the sequence listing, and exhibiting activity for (S)-1-phenethylamine, exhibiting higher activity for L-glutamic acid than that for L-alanine, and not substantially exhibiting activity for β-alanine and 4-aminobutyric acid as an amino group donor, and exhibiting higher activity for 2-ketoglutaric acid than that for pyruvic acid as an amino group receptor.

The present invention further relates to DNA encoding the polypeptide, a vector containing the DNA, and a transformant resulting from transformation with the vector.

The present invention further relates to a method for producing an optically active amino compound, comprising causing the polypeptide or a culture product of the transformant to act on a ketone compound in the presence of an amino group donor.

The present invention further relates to a method for producing an optically active amino compound, comprising causing the polypeptide or a culture product of the transformant to act on an enantiomeric mixture of amino compounds in the presence of an amino group receptor.

This description includes part or all of the content as disclosed in the description and/or drawings of Japanese Patent Application No. 2010-216546, which is a priority document of the present application.

Effects of the Invention

Isolation of a polypeptide exhibiting high activity for inexpensive glutamic acid with high solubility and generating an optically active amino compound with high optical purity, and, obtainment of a transformant with high capacity to produce the polypeptide make it possible to inexpensively and efficiently produce an optically active amino compound of interest.

EMBODIMENTS FOR CARRYING OUT THE INVENTION

The present invention is described in detail below. In addition, gene manipulation such as DNA isolation, vector construction, and transformation, which is described in detail in the Description, can be performed by methods described in a reference such as "Molecular Cloning 2nd Edition (Cold Spring Harbor Laboratory Press, 1989), Current Protocols in Molecular Biology (Greene Publishing Associates and Wiley-Interscience)" unless otherwise specified. Also, regarding the unit of enzyme activity, the amount of an enzyme that gives 1 μmol of a product per minute is designated as 1 U, unless otherwise specified.

1. Physico-Chemical Properties of the Polypeptide of the Present Invention

The polypeptide of the present invention is a polypeptide having the following physico-chemical properties.
(1) Function: It catalyzes transamination by acting on 1-benzyl-3-pyrrolidinone in the presence of an amino group donor to generate (S)-1-benzyl-3-aminopyrrolidine with optical purity of 93% e.e. or more.
(2) Substrate specificity:
(a) Amino group donor: It exhibits activity for (S)-1-phenethylamine, exhibits higher activity for L-glutamic acid than that for L-alanine, and, does not substantially exhibit activity for β-alanine and 4-aminobutyric acid.
(b) Amino group receptor: It exhibits higher activity for 2-ketoglutaric acid than that for pyruvic acid.
(3) Optimum pH: 7.0 to 8.0
(4) Optimum temperature: 30° C. to 50° C.
(5) Thermal stability: It retains residual activity equivalent to 70% or more of total activity before treatment, when treated at pH 8.0 and 30° C. to 50° C. for 30 minutes.
(6) Molecular weight: about 48 kDa as measured by sodium dodecyl sulfate-polyacrylamide gel electrophoresis.

(Substrate Specificity Assay-1: Activity for (S)-1-phenethylamine)

The polypeptide of the present invention exhibits activity for (S)-1-phenethylamine. Here, the expression "exhibits activity" refers to that when transamination activity is determined by the following method, the amount of acetophenone generated per minute is 0.01 μmol or more, preferably 0.1 μmol or more, and more preferably 1 μmol or more with respect to 1 ml of a partially purified polypeptide solution.

The above transaminase activity can be determined by the following method (referred to as "activity assay A").

A substrate solution (0.8 mL) having the following composition is added to 0.2 mL of an enzyme solution, followed by 60 minutes of reaction at 30° C. Then 50 μL of 6N hydrochloric acid is added to stop the reaction. The reaction solution is analyzed by high performance liquid chromatography under the following conditions and then the quantity of the thus generated acetophenone is determined (hereinafter, referred to as "activity assay A").

[Activity Assay A]
[Composition of Substrate Solution]

| | |
|---|---|
| (S)-1-phenethylamine | 25 mM |
| 2-ketoglutaric acid | 25 mM |
| Pyridoxal phosphate | 2.5 mM |
| Tris•hydrochloric acid buffer (pH 8.0) | 0.1 M |

[High Performance Liquid Chromatography Analysis Conditions]
Column: Cosmosil 5C8-MS (NACALAI TESQUE, INC.)
Eluent: distilled water 2000 mL/acetonitrile 500 mL/methanol 500 ml/KH$_2$PO$_4$ 6.1 g/H$_3$PO$_4$ 2.5 g
Flow rate: 1 mL/minute
Detection: 254 nm
Column temperature: 30° C.

(Substrate Specificity Assay-2: Activity for ω-Amino Acid)

The polypeptide of the present invention does not substantially exhibit activity when β-alanine, 4-aminobutyric acid, 5-aminovaleric acid, 6-aminocaproic acid, ±2,4-diaminobutyric acid, L-ornithine, L-lysine, or putrescine is used as an amino group donor. Here, the expression "does not substantially exhibit activity" refers to a case in which, when transamination activity is determined by the following method using the above amino compound as an amino group donor, the activity is 1/100 or less, preferably 1/1000 or less, and further preferably 1/10000 or less of that determined using (S)-1-phenethylamine.

Transaminase activity when the above amino group donors are used can be determined by the following method.

Each reagent is added to 100 μL of an enzyme solution so that the final concentration is as specified in the following composition of the substrate solution, and thus 400 μL of a reaction solution is prepared. After 60 minutes of reaction at 30° C., 20 μL of 3N hydrochloric acid is added to stop the reaction. Next, 80 μL of a 0.2 M aqueous sodium carbonate solution and 200 μL of an acetone solution of 3.3 mg/mL Dabsyl chloride are separately added to 20 μL of the thus obtained reaction solution, followed by 10 minutes of reaction at 70° C. Acetic acid (20 μL) is added to 50 μL of the reaction solution and then the solution is stirred. Analysis was conducted by high performance liquid chromatography under the following conditions, and then the quantity of dabsylated glutamic acid is determined. In addition, the activity of each enzyme to be used herein is adjusted so that the amount of glutamic acid generated is 2.8 mM or less as determined by the determination method.

[Composition of Substrate Solution]

| Various amino compounds | 14 mM |
|---|---|
| 2-ketoglutaric acid | 14 mM |
| Pyridoxal phosphate | 0.5 mM |
| Potassium phosphate buffer (pH 7.0) | 0.1 M |

[High Performance Liquid Chromatography Analysis Conditions]
Column: YMC-Pack Pro C18 RS (YMC)
Eluent: acetonitrile/45 mM acetate buffer (pH 4.1)=35/65 (volume ratio)
Flow rate: 0.9 mL/minute
Detection: 254 nm
Column temperature: 30° C.

(Substrate Specificity Assay-3: Activity for 2-Ketoglutaric Acid and Pyruvic Acid)

The polypeptide of the present invention exhibits activity for pyruvic acid as an amino group receptor instead of 2-ketoglutaric acid and exhibits higher activity for 2-ketoglutaric acid as an amino group receptor than that for pyruvic acid. The expression "exhibits higher activity for 2-ketoglutaric acid as an amino group receptor than that for pyruvic acid" refers to a case in which when activity is determined by the above "activity assay A" using pyruvic acid as an amino group receptor instead of 2-ketoglutaric acid, transamination activity is ½ or less and desirably ⅕ or less of that determined using 2-ketoglutaric acid as an amino group receptor.

(Substrate Specificity Assay-4: Activity for L-alanine and L-glutamic Acid)

The polypeptide of the present invention exhibits higher activity for L-glutamic acid as an amino group donor than that for L-alanine. The expression "exhibits higher activity for L-glutamic acid as an amino group donor than that for L-alanine" refers to a case in which when transamination activity is determined by the following method using L-glutamic acid as an amino group donor, transamination activity is 2 or more times, desirably 5 or more times, and more desirably 10 or more times as high as the activity determined using L-alanine as an amino group donor.

Transaminase activity when the above amino group donor is used can be determined by the following method.

Each reagent is added to 200 μL of an enzyme solution so that the final concentrations are as specified in the following composition of the substrate solution, and thus 400 μL of a reaction solution is prepared. After 90 minutes of reaction at 30° C., 15 μL of 6N hydrochloric acid is added to stop the reaction. Next, the thus obtained reaction solution is analyzed by high performance liquid chromatography under the following conditions.

[Composition of Substrate Solution]

| 1-benzyl-3-pyrrolidinone | 29 mM |
|---|---|
| Various amino compounds | 290 mM |
| Pyridoxal phosphate | 0.5 mM |
| Potassium phosphate buffer (pH 7.0) | 0.1 M |

[High Performance Liquid Chromatography Analysis Conditions]
Column: Finepak SIL C18-T (JASCO Corporation)
Eluent: distilled water 945 mL/acetonitrile 555 mL/KH$_2$PO$_4$ 7.5 g/SDS 2.16 g (adjusted with H$_3$PO$_4$ to pH 3.6)
Flow rate: 1 mL/minute
Detection: 254 nm
Column temperature: 40° C.

(Method for Determining Stereoselectivity for 1-benzyl-3-pyrrolidinone)

The polypeptide of the present invention exhibits activity to catalyze transamination by acting on 1-benzyl-3-pyrrolidinone in the presence of an amino group donor to generate (S)-1-benzyl-3-aminopyrrolidine with optical purity of 93% e.e. or more, preferably 95% e.e. or more, more preferably 97% e.e. or more, and most preferably 98% e.e. or more.

Transaminase activity when the above amino group donor is used can be determined by the following method.

Each reagent is added to 200 μL of an enzyme solution so that the final concentration is as specified in the following composition of the substrate solution, and thus 400 μL of a reaction solution is prepared. After 90 minutes of reaction at 30° C., 15 μL of 6N hydrochloric acid is added to stop the reaction. Next, the thus obtained reaction solution is analyzed by high performance liquid chromatography under the following conditions.

[Composition of Substrate Solution]

| 1-benzyl-3-pyrrolidinone | 57 mM |
|---|---|
| (S)-1-phenethylamine | 57 mM |
| Pyridoxal phosphate | 0.5 mM |
| Potassium phosphate buffer (pH 7.0) | 0.1 M |

[High Performance Liquid Chromatography Analysis Conditions]
<Quantitative Analysis>
Column: Finepak SIL C18-T (JASCO Corporation)
Eluent: distilled water 945 mL/acetonitrile 555 mL/KH$_2$PO$_4$ 7.5 g/SDS 2.16 g (adjusted with H$_3$PO$_4$ to pH 3.6)
Flow rate: 1 mL/minute
Detection: 254 nm
Column temperature: 40° C.
<Analysis of Optical Purity>
A reaction solution is treated with an appropriate amount of sodium carbonate so that it became basic, derivatized with dinitrobenzoyl chloride, and then analyzed under the following conditions.
Column: Chiralcel IA (Daicel Corporation)
Eluent: hexane/ethanol/diethylamine/acetonitrile=800/200/1/5 (volume ratio)
Flow rate: 0.8 mL/minute
Detection: 254 nm
Column temperature: 30° C.

(Optimum pH)

The optimum pH for transamination can be determined by determining transamination activity at pH ranging from pH 4.0 to 10 as described in the above "activity assay A". In the above assay, the following buffer is used for a substrate solution depending on pH at which assay is performed. The term "optimum pH" refers to pH at which the highest activity is shown in the above assay.

pH 4.0 to 6.0:0.1 M sodium acetate buffer
pH 6.0 to 8.5:0.1 M potassium phosphate buffer
pH 8.0 to 9.0:0.1 M tris-hydrochloric acid buffer
pH 9.0 to 10:0.1 M sodium carbonate buffer (Optimum Temperature)

Regarding the optimum temperature for transamination, transamination activity is determined as described in the above "activity assay A" at temperatures ranging from 30° C. to 70° C. and then the temperature at which the highest activity level is observed is defined as the optimum temperature for transamination.

(Thermal Stability)

The thermal stability of the polypeptide is determined as follows. In 0.5 mM pyridoxal phosphate and 0.1 M potassium phosphate buffer (pH 8.0), the polypeptide is treated at a temperature between 30° C. and 70° C. for 30 minutes, and then transamination activity is determined as described in the above "activity assay A." The polypeptide can be said to have thermal stability if it exhibits, after heat treatment, residual activity equivalent to 70% or more of the activity before heat treatment (designated as 100%).

(Molecular Weight)

The molecular weight of the polypeptide is calculated through comparison with the electrophoretic mobility of a standard protein measured by sodium dodecyl sulfate-polyacrylamide gel electrophoresis using 10% polyacrylamide gel.

2. Isolation of the Polypeptide of the Present Invention

Examples of the polypeptide of an embodiment of the present invention include any polypeptide, as long as it exhibits the above properties. For example, the polypeptide can be obtained from a microorganism belonging to the genus *Arthrobacter*. Examples of such a microorganism that serves as an origin of the polypeptide of an embodiment of the present invention include preferably *Arthrobacter* sp. that can be easily obtained by persons skilled in the art from public coordinated collections of microorganisms (e.g., NBRC), and further preferably, *Arthrobacter* sp. KNK04-25. The *Arthrobacter* sp. KNK04-25 was deposited under accession No. NITE P-954 on Jun. 11, 2010 with the NITE Biological Resource Center (NBRC) (NITE: the National Institute of Technology and Evaluation) (2-5-8 Kazusa Kamatari, Kisarazu, Chiba, Japan, 292-0818) and then transferred on Sep. 12, 2011 under accession No. NITE BP-954 from NITE P-954.

(Medium Components)

As a culture medium for a microorganism having the polypeptide of the present invention, a general liquid nutritional medium containing a carbon source, a nitrogen source, an inorganic salt, an organic nutrient, and the like can be used, as long as the microorganism grows therein.

In addition, when the microorganism is cultured, as an inducer for the polypeptide, an amino compound such as propylamine, 1-butyl amine, 2-butyl amine, 2-pentylamine, isopropylamine, isobutyl amine, 7-methoxy-2-aminotetralin, 1-phenethylamine, and 1-benzyl-3-aminopyrrolidine can be added to a medium, and then the microorganism can be cultured. The inducer may be used independently or 2 or more types of inducer may be mixed and then used. The amount of the inducer to be added herein is not particularly limited, but is preferably, in view of inhibition of microbial growth, generally 1% by weight or less in a general medium composition. The time for adding the above inducer is not particularly limited and the inducer may be added at the start of culture or during culture. Furthermore, to enhance the effect of the inducer, a fewer amount of a general carbon source, nitrogen source, inorganic salt, or organic nutrient other than the inducer can be effective in some cases.

(Purification of Polypeptide)

The polypeptide of an embodiment of the present invention can be purified from a microorganism that produces the polypeptide by a protein purification method known by persons skilled in the art. For example, cells are collected by centrifugation or filtration from culture solutions of the microorganism, the thus obtained cells are disrupted by a physical technique using an ultrasonic disintegrator, glass beads, or the like, cell residues are removed by centrifugation to prepare a cell-free extract, the cell-free extract is subjected to fractional precipitation, ion exchange chromatography, hydrophobic chromatography, gel filtration chromatography, reverse phase chromatography, ultrafiltration, or the like, and thus the polypeptide can be isolated.

3. The Amino Acid Sequence of the Polypeptide of the Present Invention

Examples of the polypeptide of the present invention include the following polypeptides (a) to (g):

(a) a polypeptide consisting of the amino acid sequence shown in SEQ ID NO: 1 in the sequence listing;

(b) a polypeptide consisting of an amino acid sequence that has a deletion, a substitution, an insertion, or an addition of 1 or more amino acids with respect to the amino acid sequence shown in SEQ ID NO: 1 in the sequence listing, and having activity to act on 1-benzyl-3-pyrrolidinone in the presence of an amino group donor to generate (S)-1-benzyl-3-aminopyrrolidine with optical purity of 93% e.e. or more;

(c) a polypeptide consisting of an amino acid sequence that has a deletion, a substitution, an insertion, or an addition of 1 or more amino acids with respect to the amino acid sequence shown in SEQ ID NO: 1 in the sequence listing, and exhibiting activity for (S)-1-phenethylamine, exhibiting higher activity for L-glutamic acid than that for L-alanine, and not substantially exhibiting activity for β-alanine and 4-aminobutyric acid as an amino group donor, and having higher activity for 2-ketoglutaric acid than that for pyruvic acid as an amino group receptor;

(d) a polypeptide consisting of an amino acid sequence that has a deletion, a substitution, an insertion, or an addition of 1 or more amino acids with respect to the amino acid sequence shown in SEQ ID NO: 1 in the sequence listing, having an optimum pH ranging from 7.0 to 8.0, having an optimum temperature ranging from 30° C. to 50° C., retaining residual activity equivalent to 70% or more of the activity before treatment when treated at 30° C. to 50° C. for 30 minutes, and having a molecular weight of about 48 kDa as measured by sodium dodecyl sulfate-polyacrylamide gel electrophoresis;

(e) a polypeptide consisting of an amino acid sequence that has 50% or more sequence identity with the amino acid sequence shown in SEQ ID NO: 1 in the sequence listing, and having activity to act on 1-benzyl-3-pyrrolidinone in the presence of an amino group donor to generate (S)-1-benzyl-3-aminopyrrolidine with optical purity of 93% e.e. or more;

(f) a polypeptide consisting of an amino acid sequence that has 50% or more sequence identity with the amino acid sequence shown in SEQ ID NO: 1 in the sequence listing, and exhibiting activity for (S)-1-phenethylamine, exhibiting higher activity for L-glutamic acid than that for L-alanine, and not substantially exhibiting activity for β-alanine or 4-aminobutyric acid as an amino group donor and, having higher activity for 2-ketoglutaric acid than that for pyruvic acid as an amino group receptor; and (g) a polypeptide consisting of an amino acid sequence that has 50% or more sequence identity with the amino acid sequence shown in SEQ ID NO: 1 in the sequence listing, having an optimum pH ranging from 7.0 to 8.0, having an optimum temperature ranging from 30° C. to 50° C., retaining residual activity equivalent to 70% or more of the activity before treatment when treated at 30° C. to 50° C. for 30 minutes and having a molecular weight of about 48 kDa as measured by sodium dodecyl sulfate-polyacrylamide gel electrophoresis.

An example of the amino acid sequence of the polypeptide of the present invention is the amino acid sequence shown in SEQ ID NO: 1 in the sequence listing, which is encoded by the nucleotide sequence shown in SEQ ID NO: 2 in the sequence listing.

A polypeptide consisting of an amino acid sequence that has a deletion, a substitution, an insertion, or an addition of 1 or more amino acids with respect to the amino acid sequence shown in SEQ ID NO: 1 in the sequence listing can be prepared according to a known method described in Current Protocols in Molecular Biology (John Wiley and Sons, Inc., 1989) or the like. The thus prepared polypeptide is included in the above polypeptide as long as it has the above various physico-chemical properties.

In the amino acid sequence shown in SEQ ID NO: 1 in the sequence listing, site(s) to be subjected to deletion, substitution, insertion, or addition of an amino acid(s) are not particularly limited, but a highly conserved region is preferably avoided. Here, the term "highly conserved region" refers to a position at which amino acids match among a plurality of sequences when the amino acid sequences of a plurality of enzymes (polypeptides) from different origins are optimally aligned and compared. Such a highly conserved region can be confirmed by comparing the amino acid sequence shown in SEQ ID NO: 1 with the amino acid sequence of transaminase (polypeptide) derived from another microorganism described above, using a tool such as GENETYX.

An amino acid sequence modified by deletion, substitution, insertion, or addition may contain only 1 type of modification (e.g., substitution), or 2 or more types of modification (e.g., substitution and insertion). In the case of substitution, an amino acid(s) to be substituted is preferably an amino acid (homologous amino acid) having properties analogous to those of an amino acid before substitution. Here, amino acids within the same group are regarded as homologous amino acids.

(Group 1: Neutral non-polar amino acid) Gly, Ala, Val, Leu, Ile, Met, Cys, Pro, Phe
(Group 2: Neutral polar amino acid) Ser, Thr, Gln, Asn, Trp, Tyr
(Group 3: Acidic amino acid) Glu, Asp
(Group 4: Basic amino acid) His, Lys, Arg.

The term "(one or) more amino acids" above refers to 60, preferably 20, more preferably 15, further preferably 10, and further preferably 5, 4, 3, or 2 or less amino acids, for example.

Sequence identity with the amino acid sequence shown in SEQ ID NO: 1 in the sequence listing is preferably 50% or more, more preferably 70% or more, further preferably 80% or more, further more preferably 85% or more, still further more preferably 90% or more, and most preferably 95% or more.

The sequence identity of an amino acid sequence is represented by a value obtained by comparing the amino acid sequence shown in SEQ ID NO: 1 in the sequence listing with an amino acid sequence to be evaluated, dividing the number of positions at which amino acids of the two sequences match by the total number of amino acids compared, and then multiplying the result by 100.

An additional amino acid sequence can be bound to the amino acid sequence shown in SEQ ID NO: 1 as long as the polypeptide has activity to act on 1-benzyl-3-pyrrolidinone in the presence of an amino group donor to generate (S)-1-benzyl-3-aminopyrrolidine with optical purity of 93% e.e. or more. For example, a tag sequence such as a histidine tag or an HA tag can be added. Alternatively, the polypeptide of the present invention can be fused to another protein to prepare a fusion protein. Also, the polypeptide of the present invention may be a peptide fragment as long as it has the above transamination activity.

4. Cloning of DNA Encoding the Polypeptide of the Present Invention

The DNA of the present invention encodes the above polypeptide. The DNA may be any DNA that can express the polypeptide within host cells into which it is introduced according to a method described later, and may contain an arbitrary untranslated region. Persons skilled in the art can easily obtain the DNA of the present invention based on SEQ ID NO: 2 in the sequence listing by a chemical synthesis method. Regarding another method, persons skilled in the art can obtain the DNA from a microorganism serving as an origin of the polypeptide by a known method, as long as the purified polypeptide can be obtained by the known method.

As a method for obtaining DNA in an embodiment of the present invention, an example using the above *Arthrobacter* sp. KNK04-25 is described below, but the method to be employed in the present invention is not limited thereto.

First, the above polypeptide purified from a cell-free extract of the microorganism is digested with appropriate endopeptidase, fragments cleaved by reverse phase HPLC are purified, and then a portion of or the entire amino acid sequence is determined using a "type PPSQ-33A full automatic protein primary structure analyzer (Shimadzu Corporation)," for example. Based on the thus obtained amino acid sequence information, PCR (Polymerase Chain Reaction) primers for amplification of a portion of DNA encoding the polypeptide are synthesized. Next, the chromosomal DNA of a microorganism serving as an origin of the polypeptide is prepared by a general DNA isolation method such as a method of Visser et al. ((Appl. Microbiol. Biotechnol., 53, 415 (2000)). PCR is performed using the chromosomal DNA as a template and the above-mentioned PCR primers, a portion of DNA encoding the polypeptide is amplified, and thus the nucleotide sequence thereof is determined. The nucleotide sequence can be determined using a "type ABI3100 DNA Sequencer (Applied Biosystems)," for example.

If the nucleotide sequence of a portion of DNA encoding the polypeptide is revealed, for example, the entire sequence can be determined by an inverse PCR method (Nucl. Acids Res., 16, 8186 (1988)).

An example of the thus obtained DNA of the polypeptide is DNA containing the nucleotide sequence shown in SEQ ID NO: 2 in the sequence listing.

The nucleotide sequence shown in SEQ ID NO: 2 in the sequence listing is as described below.

5. The Nucleotide Sequence of DNA Encoding the Polypeptide of the Present Invention Examples of DNA encoding the polypeptide of the present invention include the following DNAs (A) to (C):

(A) DNA consisting of the nucleotide sequence shown in SEQ ID NO: 2 in the sequence listing;
(B) DNA hybridizing under stringent conditions to DNA consisting of a nucleotide sequence complementary to the nucleotide sequence shown in SEQ ID NO: 2 in the sequence listing;
(C) DNA consisting of a nucleotide sequence that has a deletion, a substitution, an insertion, or an addition of 1 or more nucleotides with respect to the nucleotide sequence shown in SEQ ID NO: 2 in the sequence listing.

Here, the expression "DNA hybridizing under stringent conditions to DNA consisting of a nucleotide sequence complementary to the nucleotide sequence shown in SEQ ID NO: 2 in the sequence listing" refers to DNA that is obtained by a colony•hybridization method, a plaque•hybridization method, a Southern hybridization method, or the like under stringent conditions using DNA as a probe consisting of a nucleotide sequence complementary to the nucleotide sequence shown in SEQ ID NO: 2 in the sequence listing.

Hybridization can be performed according to the method described in "Molecular Cloning, A laboratory manual, second edition (Cold Spring Harbor Laboratory Press, 1989)" or the like. Here, the term "DNA hybridizing under stringent conditions" refers to DNA that can be obtained by performing hybridization at 65° C. in the presence of 0.7 to 1.0 M NaCl using a filter to which colony- or plaque-derived DNA has been immobilized, and then washing the filter at 65° C. using a 2×SSC solution (the composition of a 1×SSC solution: 150 mM sodium chloride and 15 mM sodium citrate). Furthermore the term refers to DNA that can be obtained by washing preferably with a 0.5×SSC solution at 65° C., more preferably with a 0.2×SSC solution at 65° C., and further preferably with a 0.1×SSC solution at 65° C.

Hybridization conditions are as described above, but are not particularly limited to these conditions. Elements affecting hybridization stringency may be a plurality of elements such as temperature and salt concentration. Persons skilled in the art can realize the optimum stringency by adequately selecting these elements.

An example of DNA capable of hybridizing under the above conditions is DNA having 70% or more, preferably 75% or more, more preferably 80% or more, further more preferably 85% or more, and most preferably 90% or more sequence identity with the DNA shown in SEQ ID NO: 2. As long as the polypeptide encoded by such DNA has the above transamination activity, it is included in examples of the above DNA.

The sequence identity (%) of DNA is represented by a numerical value obtained by optimally aligning two DNAs to be compared, dividing the number of positions at which nucleobases match (e.g., A, T, C, G, U, or I) between the two sequences by the total number of nucleotides compared, and then multiplying the result by 100.

DNA sequence identity can be calculated using the following sequencing tool, for example: GCG Wisconsin Package (Program Manual for The Wisconsin Package, Version 8, September 1994, Genetics Computer Group, 575 Science Drive Medison, Wisconsin, U.S.A. 53711; Rice, P. (1996) Program Manual for EGCG Package, Peter Rice, The Sanger Centre, Hinxton Hall, Cambridge, CB10 1RQ, England), and, the ExPASy World Wide Web Molecular Biology Server (Geneva University Hospital and University of Geneva, Geneva, Switzerland).

Here, the term "DNA that has a deletion, a substitution, an insertion, or an addition of 1 or more nucleotides with respect to the nucleotide sequence shown in SEQ ID NO: 2 in the sequence listing" can be prepared according to a known method described in "Current Protocols in Molecular Biology (John Wiley and Sons, Inc., 1989)," for example.

A site(s) of the nucleotide sequence shown in SEQ ID NO: 2 in the sequence listing, which is subjected to deletion, substitution, insertion, or addition of a nucleotide(s) is not particularly limited. Preferably a highly conserved region is avoided to prevent frame shift from taking place. Here, the term "highly conserved region" refers to a position(s) at which nucleotides match among a plurality of sequences when the nucleotide sequences of a plurality of polypeptides from different origins are optimally aligned and compared. Such a highly conserved region can be confirmed by comparing the nucleotide sequence shown in SEQ ID NO: 2 with the nucleotide sequence of a transaminase gene derived from a known microorganism using a tool such as GENETYX.

A nucleotide sequence modified by deletion, substitution, insertion, or addition may contain only 1 type of modification (e.g., substitution) or 2 or more types of modification (e.g., substitution and insertion).

The above term "(one or) more nucleotides" refers to 150, preferably 100, more preferably 50, further preferably 20, 10, 5, 4, 3, or 2 or less nucleotides, for example.

6. Vector

Vector DNA to be used for introducing the DNA of an embodiment of the present invention into a host microorganism and then causing the expression of the DNA in the host microorganism may be any vector that enables expression of the polypeptide encoded by the DNA within an appropriate host microorganism. Examples of such vector DNA include a plasmid vector, a phage vector, and a cosmid vector. Furthermore, a shuttle vector that enables gene exchange with another host strain can be used herein.

Such a vector contains a regulatory factor of an operably linked promoter (e.g., lacUV5 promoter, trp promoter, trc promoter, tac promoter, lpp promoter, tufB promoter, recA promoter, and pL promoter) can be preferably used as a vector containing an expression unit operably linked to the DNA of the present invention. Examples thereof include pUC18 (Toyobo Co., Ltd.), pUC19 (Toyobo Co., Ltd.), and pUCNT (International Publication WO94/03613).

The term "regulatory factor" refers to a nucleotide sequence having a functional promoter and an arbitrary related transcriptional element (e.g., enhancer, CCAAT box, TATA box, and SPI site).

Furthermore, the term "operably linked" refers to that various regulatory elements regulating gene expression such as a promoter and an enhancer are ligated to a gene so that they can function within the host cells. Types and kinds of regulatory factor can be varied depending on host, which is a matter known by persons skilled in the art.

Vectors, promoters, and the like that can be used in various organisms are specifically described in "Basic Microbiology (Biseibutsu-gaku Kiso-ko-za) 8 genetic engineering (KYORITSU SHUPPAN CO., LTD, 1987)," for example.

7. Host and Transformant

Host organisms to be used for expressing the DNA of an embodiment of the present invention are not particularly limited, as long as they are organisms that are transformed with an expression vector containing DNA encoding each polypeptide and can express the polypeptide in which the DNA has been introduced. Examples of microorganisms that can be used herein include bacteria for which host vector systems have been developed, such as bacteria of the genus *Escherichia*, the genus *Bacillus*, the genus *Pseudomonas*, the genus *Serratia*, the genus *Brevibacterium*, the genus *Corynebacterium*, the genus *Streptococcus*, or the genus *Lactobacillus*, actinomycetes for which host vector systems have been developed, such as those of the genus *Rhodococcus* or the genus *Streptomyces*, yeast for which host vector systems have been developed such as that of the genus *Saccharomyces*, the genus *Kluyveromyces*, the genus *Schizosaccharomyces*, the genus *Zygosaccharomyces*, the genus *Yarrowia*, the genus *Trichosporon*, the genus *Rhodosporidium*, the genus *Pichia*, or the genus *Candida*, and molds for which host vector systems have been developed such as those of the genus *Neurospora*, the genus *Aspergillus*, the genus *Cephalosporium*, or the genus *Trichoderma*. Furthermore, various host·vector systems have been developed for plants and animals other than microorganisms. Systems for expressing heteroproteins in large amounts in particularly insects (such as silkworm) (Nature 315, 592-594 (1985)) or plants such as rapeseed, corn, or potato have been developed and can be appropriately used. Of these, bacteria are preferred in terms of introduction and expression efficiency and *Escherichia coli* is particularly preferred.

A vector for expressing a polypeptide containing the DNA of the present invention can be introduced into a host microorganism by a known method. For example, when *Escherichia coli* is used as a host microorganism, the vector can be introduced into host cells using commercially available *E. coli* HB101 competent cells (Takara Bio Inc.).

8. Method for Producing an Optically Active Amino Compound

Next, a method for producing an optically active amino compound using the polypeptide of an embodiment of the present invention or a microorganism capable of producing the polypeptide is as described below.

Examples of a microorganism capable of producing the polypeptide of an embodiment of the present invention include the above *Arthrobacter* sp. KNK04-25 and a transformant in which a vector containing the DNA of an embodiment has been introduced.

Examples of the method for producing an optically active amino compound of the present invention include a method (hereinafter, referred to as "production method I") that involves transferring an amino group from an amino group donor to a ketone compound having the same backbone as that of an amino compound of interest, and collecting the thus generated optically active amino compound and a method (hereinafter, referred to as "production method II") that involves selectively transferring, from an enantiomeric mixture of amino compounds, an amino group (of either one of enantiomers) to an amino group receptor and then collecting the remaining enantiomer (optically active amino compound).

First, the production method I is as described below.

(Production Method I)

The production method I comprises causing the polypeptide of the present invention or the culture product of a transformant capable of producing the polypeptide of the present invention to act on a ketone compound in the presence of an amino group donor, so as to produce an optically active amino compound.

The production method comprises causing

[Chemical formula 1]

the polypeptide or the culture product of a microorganism capable of producing the polypeptide to act on a ketone compound represented by general formula (1) in the presence of an amino group donor,

[Chemical formula 2]

to produce an optically active amino compound represented by general formula (2), for example.

In formulae (1) and (2) above, $R^1$ and $R^2$ denote alkyl groups that may be substituted, aralkyl groups that may be substituted or aryl groups that may be substituted, and $R^1$ and $R^2$ may bind to each other to form a ring. However, $R^1$ and $R^2$ are structurally different.

$R^1$ and $R^2$ are preferably C1-20 alkyl groups that may be substituted, aralkyl groups that may be substituted, or aryl groups that may be substituted, and are more preferably C1-10 alkyl groups that may be substituted, aralkyl groups that may be substituted, or aryl groups that may be substituted.

Examples of an aryl group include a phenyl group, a naphthyl group, a pyridyl group, a thienyl group, an oxadiazolyl group, an imidazolyl group, a thiazolyl group, a furyl group, a pyrrolyl group, a phenoxy group, a naphthoxy group, a pyridyloxy group, a thienyloxy group, an oxadiazolyloxy group, an imidazolyloxy group, a thiazolyloxy group, a furyloxy group, and a pyrrolyloxy group. Examples of an alkyl group include a methyl group, an ethyl group, a propyl group, a butyl group, a pentyl group, a hexyl group, an isopropyl group, a sec-butyl group, a tert-butyl group, a methoxy group, an ethoxy group, a tert-butoxy group, a methoxycarbonyl group, an ethoxycarbonyl group, a tert-butoxycarbonyl group, a vinyl group, an allyl group, a cyclopentyl group, a cyclohexyl group, and a cycloheptyl group. Examples of an aralkyl group include a benzyl group and the like.

These groups may be further substituted. Examples of a substituent include a halogen atom, a nitrogen atom, a sulfur atom, a hydroxy group, a nitro group, a cyano group, a methoxy group, an ethoxy group, a carboxyl group, a carboxymethyl group, a carboxyethyl group, and a methylenedioxy. Furthermore, a ring may be formed via a substituent.

Specific examples of the above ketone compound include 1-tetralone, 2-tetralone, 5-methoxy-2-tetralone, 6-methoxy-2-tetralone, 7-methoxy-2-tetralone, 8-methoxy-2-tetralone, 1-benzyl-3-pyrrolidinone, 1-Boc-3-pyrrolidinone, 1-Cbz-3-pyrrolidinone, 1-benzyl-3-piperidinone, 1-Boc-3-piperidinone, 1-Cbz-3-piperidinone, acetophenone, and 3,4-dimethoxyphenyl acetone.

(Amino Group Donor)

As an amino group donor, any amino group donor can be used as long as it is an amine compound on which the polypeptide of the present invention acts. Specific examples thereof include 1-phenethylamine, 2-butylamine, 2-pentylamine, 2-heptylamine, 3-heptylamine, n-ethylamine, n-propylamine, n-butylamine, n-amylamine, isopropylamine, isobutylamine, glycine, alanine, glutamic acid, 3-amino-1-phenylbutane, benzylamine, β-phenethylamine, cyclohexylamine, and optically active compounds thereof. Of these, 1-phenethylamine is preferred and particularly glutamic acid is preferred since it is inexpensive and has high solubility.

(Form of Polypeptide)

In the production method I, the polypeptide of the present invention or the culture product of a microorganism capable of generating the polypeptide is caused to act on the ketone compound in the presence of an amino group donor.

Here, the term "culture product" refers to a culture solution containing cells, cultured cells, or a processed product thereof. Here, the term "processed product thereof" refers to, for example, a cell-free extract, lyophilized cells, acetone-dried cells, or a pulverized product of cells. Moreover, the polypeptides and culture products thereof can be used in the form of immobilized polypeptides or immobilized cells obtained by known means. Immobilization can be performed by a method known by persons skilled in the art (e.g., a crosslinking method, a physical adsorption method, or an integrated immobilization method).

(Improvement of Reactivity by Solving the Reaction Equilibrium Problem and the Product Inhibition)

Amination using transamination is generally a reversible reaction, so that in general it apparently stops at an equilibrium point. A reaction using the polypeptide of the present invention can be improved by combining known methods for solving such reaction equilibrium problem.

For example, an effective method for solving the reaction equilibrium problem involves using alanine as an amino group donor, conjugating lactate dehydrogenase and glucose dehydrogenase for coenzyme regeneration, and converting pyruvic acid to be produced as a by-product to lactic acid that does not act on transaminase, as described in WO2007/139055A. Similarly, examples of an effective method include a method that involves using alanine as an amino group donor and removing pyruvic acid to be produced as a by-product with pyruvate decarboxylase (WO2007/093372A1), a method using alanine dehydrogenase (US2009/0117627A1, Evonik Degussa GmbH), a method using hydrogen peroxide for removal (US2008/0213845A1), and a method using acetobutyrate synthase (Biosci. Biotechnol. Biochem. 72(11), 3030-3033 (2008)).

Alternatively, an effective method involves using glutamic acid as an amino group donor, conjugating mandelate dehydrogenase or hydroxyisocaproate dehydrogenase with glucose dehydrogenase or formate dehydrogenase for coenzyme regeneration, and converting 2-ketoglutaric acid to be produced as a by-product to 2-hydroxyglutaric acid that does not act on transaminase, thereby solving the reaction equilibrium problem. Similarly, an effective method involves using glutamic acid as an amino group donor, conjugating glutamate dehydrogenase with glucose dehydrogenase or formate dehydrogenase for coenzyme regeneration, and thus converting 2-ketoglutaric acid to be produced as a by-product to glutamic acid, thereby solving the reaction equilibrium problem.

Furthermore, these techniques are effective means for solving not only the reaction equilibrium problem, but also the product inhibition caused by a ketone compound to be produced as a by-product from an amino group donor.

(Substrate Concentration)

Regarding the concentration of a substrate to be used for reaction, the concentration of a ketone compound ranges from 0.1% by weight to 80% by weight and preferably ranges from 1% by weight to 50% by weight in the composition of a reaction solution. Moreover, in the case of chiral amine, an amino group donor is preferably used so that the concentration ranges from 80 mol % to 1200 mol %, and preferably 100 mol % to 600 mol % with respect to that of a ketone compound. In addition, when a racemic amino compound is used as the above amino group donor, it can be used so that the concentration of one of the racemic compounds is as described above.

(Reaction pH)

Regarding the pH for the polypeptide of the present invention to act, the lower limit thereof is preferably pH 6.0 or more, and more preferably pH 7.0 or more, and the upper limit thereof is preferably pH 9.0 or less and more preferably pH 8.0 or less, in view of the optimum pH of the polypeptide. When a plurality of polypeptides (enzymes) are conjugated, pH at which all enzymes to be used herein can stably and highly actively act is preferably selected.

(Reaction Temperature)

Regarding the temperature for the polypeptide of the present invention to act, it is preferably 25° C. or higher, more preferably 30° C. or higher, preferably 60° C. or lower, and more preferably 50° C. or lower in view of optimum temperature and thermal stability of the polypeptide. When a plurality of polypeptides (enzymes) are conjugated, the reaction temperature at which all enzymes to be used herein stably and highly actively act is preferably selected.

(Solvent)

As a reaction solvent, an aqueous medium such as ion exchanged water or buffer is generally used. Reaction can also be performed with a system containing an organic solvent. As an organic solvent, for example, an alcohol-based solvent such as methanol, ethanol, propanol, isopropanol, and butanol, an aliphatic hydrocarbon-based solvent such as pentane and hexane, an aromatic hydrocarbon-based solvent such as benzene and toluene, a halogenated hydrocarbon-based solvent such as methylene chloride and chloroform, an ether-based solvent such as diethyl ether and diisopropylether, an ester-based solvent such as ethyl acetate and butyl acetate, a ketone-based solvent such as acetone and methyl ethyl ketone, or another solvent such as acetonitrile can be adequately used.

(2-Phase System)

If necessary, the above organic solvent is added to water to a level exceeding its solubility to water and then reaction can be performed with the 2-phase system. An organic solvent is also caused to coexist in such a reaction system, so that selectivity, conversion rate, yield, and the like are improved in many cases.

(Reaction Time)

The time for reaction generally ranges from 1 hour to 1 week and preferably ranges from 1 to 72 hours. Reaction conditions under which reaction is completed within such reaction duration are preferably selected.

(Extraction and Purification)

An optically active amino compound is generated by the above reaction. The thus generated optically active amino compound can be isolated from a reaction mixture by a known method such as extraction, distillation, recrystallization, and column separation.

For example, after adjustment of pH to acidic, an unreacted substrate and a ketone compound (resulting from transamination) corresponding to an amino group donor can be selectively removed with the use of a general solvent (e.g., an ether-based solvent such as diethyl ether and diisopropylether, an ester-based solvent such as ethyl acetate and butyl acetate, a hydrocarbon-based solvent such as hexane, octane, and benzene, and a halogenated hydrocarbon-based solvent such as methylene chloride), while leaving an optically active amino compound generated in an aqueous phase. The thus generated optically active amino compound and unreacted amino group donor can be extracted similarly with a general organic solvent after adjustment of the pH to basic, for example. The thus generated optically active amino compound and unreacted amino group donor can be separated by distillation, for example.

Next, the production method II of the present invention is as described below.

(Production Method II)

The production method is a method for producing an optically active amino compound, comprising causing the polypeptide of the present invention or the culture product of a transformant capable of producing the polypeptide of the present invention to act on an enantiomeric mixture of amino compounds in the presence of an amino group receptor.

According to the production method, for example,

[Chemical formula 3]

(3)

the polypeptide or the culture product of a microorganism capable of producing the polypeptide is caused to act on an enantiomeric mixture of amino compounds represented by general formula (3) in the presence of an amino group receptor,

[Chemical formula 4]

(4)

so that an optically active amino compound represented by general formula (4) can be obtained.

$R^1$ and $R^2$ in the above formulae (3) and (4) are the same as $R^1$ and $R^2$ in the above formulae (1) and (2).

Specific examples of the above optically active amino compound include 1-aminotetralin, 2-aminotetralin, 5-methoxy-2-aminotetralin, 6-methoxy-2-aminotetralin, 7-methoxy-2-aminotetralin, 8-methoxy-2-aminotetralin, 1-benzyl-3-aminopyrrolidine, 1-Boc-3-aminopyrrolidine, 1-Cbz-3-aminopyrrolidine, 1-benzyl-3-aminopiperidine, 1-Boc-3-aminopiperidine, 1-Cbz-3-aminopiperidine, 1-phenethylamine, and 3,4-dimethoxyamphetamine.

(Amino Group Receptor)

In the method, a ketone compound is used as an amino group receptor. The ketone compound may be any ketone compound as long as it has activity as an amino group receptor, and is preferably, 2-ketoglutaric acid or glyoxylic acid.

In the production method II, the polypeptide of the present invention or the culture product of a transformant capable of generating the polypeptide is caused to act on an enantiomeric mixture of amino compounds in the presence of the amino group receptor.

Here, the term "an enantiomeric mixture of amino compounds" refers to a mixture of an enantiomer and its corresponding (mirror-image) enantiomer. In general, a racemic body is inexpensive and can be easily obtained, and thus such a racemic body is preferably used herein. However, examples of an enantiomeric mixture are not limited to racemic bodies. For example, with the use of a mixture containing an enantiomer in an amount slightly higher than that of its mirror-image enantiomer, the optical purity thereof can be preferably increased by the production method II.

In addition, what is meant by the culture product is similar to that in the case of the above production method I.

Furthermore, the concentration of an amino compound ranges from 0.1% by weight to 80% by weight and preferably ranges from 1% by weight to 50% by weight in the composition of a reaction solution. The concentration of an amino group receptor to be preferably employed herein ranges from 30 mol % to 100 mol %, and preferably ranges from 50 mol % to 60 mol % with respect to that of an amino compound. Regarding reaction pH, reaction temperature, and reaction solvent, conditions similar to those for the production method I can be employed.

An optically active amino compound is generated by the above reaction. The thus generated optically active amino compound can be isolated from a reaction mixture by a method similar to the production method I.

EXAMPLES

The present invention is hereafter described in greater detail with reference to the following examples, although the present invention is not limited thereto.

Example 1

Obtainment and Purification of Polypeptide Having *Arthrobacter* sp. KNK04-25-Derived Transamination Activity

*Arthrobacter* sp. KNK04-25 (NITE BP-954), which is a microorganism capable of aminating 1-benzyl-3-pyrrolidinone using (S)-1-phenethylamine as an amino group donor, was isolated from soil. The purification of a polypeptide having transamination activity to catalyze the above reaction, cloning of a structural gene thereof, and construction of a recombinant vector containing the structural gene were performed. Hereinafter, the polypeptide is referred to as "TAT."

(Transamination Activity Assay)

A substrate solution (0.8 mL) having the following composition was added to 0.2 mL of an enzyme solution, reaction was performed at 30° C. for 60 minutes, and then 50 μL of 6N hydrochloric acid was added to stop the reaction. The reaction solution was analyzed by high performance liquid chromatography under the following conditions, and then the quantity of the thus generated acetophenone was determined. Under the reaction conditions, activity by which 1 μmol of acetophenone was generated per minute was defined as 1 U.

[Composition of Substrate Solution]

| (S)-1-phenethylamine | 25 mM |
|---|---|
| 2-ketoglutaric acid | 25 mM |
| Pyridoxal phosphate | 2.5 mM |
| Tris·hydrochloric acid buffer (pH 8.0) | 0.1 M |

[High Performance Liquid Chromatography Analysis Conditions]
Column: Cosmosil 5C8-MS (NACALAI TESQUE, INC.)
Eluent: distilled water 2000 mL/acetonitrile 500 mL/methanol 500 ml/$KH_2PO_4$ 6.1 g/$H_3PO_4$ 2.5 g
Flow rate: 1 mL/minute
Detection: 254 nm
Column temperature: 30° C.

The above *Arthrobacter* sp. KNK04-25 was inoculated into 5 mL of 2YT medium (composition: 16 g/L triptone (Becton, Dickinson and Company), 10 g/L yeast extract (Becton, Dickinson and Company), 5 g/L NaCl (pH 7.0)) in a large test tube, and then cultured at 30° C. for 1 day, so that a pre-cultured solution was obtained.

Next, the thus obtained pre-cultured solution was inoculated into 3.0 L of N medium (composition: 5 g/L polypeptone (Nihon Pharmaceutical Co., Ltd.), 3 g/L D-glucose, 2 g/L NaCl, 0.2 g/L yeast extract (Becton, Dickinson and Company), 6 drops of Adekanol LG-109 (NOF Corporation), 0.5 g/L (S)-1-phenethylamine (pH 7.0)) in a 5-liter mini jar and then cultured with a ventilation amount of 0.3 vvm and the stirring rotation number of 350 rpm at 30° C. for 27 hours.

Subsequently, cells are collected from the culture solution by centrifugation and then suspended in 10 mM phosphate buffer (pH 7.0) containing 0.5 mM dithiothreitol, 0.5 mM pyridoxal phosphate, and 0.1 mM phenyl methylsulfonyl fluoride. The thus obtained suspension was subjected to disruption by ultrasonication. Next, solid material in the disrupted product was removed by centrifugation, so that a cell-free extract was prepared.

The thus obtained cell-free extract was maintained at 60° C. for 30 minutes and then the resulting precipitate was removed by centrifugation. Ammonium sulfate was added to the supernatant to give a saturation of 40%. The resultant was dissolved and then the resulting precipitate was removed by centrifugation. Ammonium sulfate was added to the supernatant to give a saturation of 70%. The resultant was dissolved and then the resulting precipitate was recovered by centrifugation.

The precipitate was dissolved in 10 mM phosphate buffer (pH 7.0) containing 0.5 mM dithiothreitol, 0.5 mM pyridoxal phosphate, and 0.1 mM phenyl methylsulfonyl fluoride, and then dialysis was performed against the buffer. The resultant was applied to a TOYOPEARL DEAE-650M (TOSOH CORPORATION) column (90 mL) equilibrated with the same buffer, so that the active fractions were adsorbed. The column was washed with the same buffer and then the active fractions were eluted with a linear gradient (0.1 M to 0.5 M) of sodium chloride.

The thus eluted active fractions were collected, ammonium sulfate was dissolved in the resultants to a final concentration of 1.5M. Each resultant was applied to a TOYOPEARL Butyl-650S (TOSOH CORPORATION) column (20 mL) equilibrated in advance with 10 mM phosphate buffer (pH 7.0) containing 1.5M ammonium sulfate, 0.5 mM dithiothreitol, 0.5 mM pyridoxal phosphate, and 0.1 mM phenyl methylsulfonyl fluoride, and then the active fractions were adsorbed. The column was washed with the same buffer and then active fractions were eluted with a linear gradient (1.0 M to 0.4 M) of ammonium sulfate. Active fractions were collected, buffer exchange with 10 mM phosphate buffer (pH 7.0) containing 0.5 mM dithiothreitol, 0.5 mM pyridoxal phosphate, and 0.1 mM phenyl methylsulfonyl fluoride was performed using a PD-10 column (GE Healthcare Japan), and thus an electrophoretically almost single purified enzyme preparation was obtained.

Example 2

Cloning of TAT Gene (Preparation of PCR Primer)

The N-terminal amino acid sequence of purified TAT obtained in Example 1 was determined using a PPSQ-33A full automatic protein primary structure analyzer (Shimadzu Corporation). Moreover, the purified TAT obtained above was altered in the presence of 8 M urea and then the resultant was digested with *Achromobacter*-derived lysyl endopeptidase (Wako Pure Chemical Industries, Ltd.). The amino acid sequence of the thus obtained peptide fragment was determined by the method similar to that used for the N-terminal amino acid sequence. In view of the nucleotide sequence predicted from the amino acid sequence, primer 1 (SEQ ID NO: 3 in the sequence listing), and, primer 2 (SEQ ID NO: 4 in the sequence listing) were synthesized for amplification of a portion of the TAT gene by PCR.

(Amplification of TAT Gene by PCR)

Chromosomal DNA was extracted from the culture solution of the *Arthrobacter* sp. KNK04-25 according to the method of Ausubel et al., (Current Protocols in Molecular Biology, 1987). PCR was performed using the thus obtained chromosomal DNA as a template and the above-synthesized primers 1 and 2. As a result, an about 450-bp DNA fragment thought to be a portion of the gene was obtained. PCR was performed under reaction conditions specified in the instruction manual using TaKaRa Ex Taq (Takara Bio Inc.) as DNA polymerase.

The nucleotide sequence of the DNA fragment was determined using an ABI PRISM Dye Terminator Cycle Sequencing Ready Reaction Kit (Applied Biosystems) and an ABI 3100 DNA Sequencer (Applied Biosystems). The nucleotide sequence is shown in SEQ ID NO: 5 in the sequence listing.

(Determination of the Full-Length Sequence of TAT Gene by Inverse-PCR Method)

The above obtained chromosomal DNA of *Arthrobacter* sp. KNK04-25 was completely digested with a restriction enzyme (Aat II, ApaL I, or Pst I). The thus obtained digest was intramolecularly cyclized using T4 DNA ligase (Takara Bio Inc.). With the use of the resultant as a template, the full nucleotide sequence of the TAT gene on the chromosomal DNA was determined by the inverse-PCR method based on the above-found partial nucleotide sequence information of the TAT gene (Nucl. Acids Res., 16, 8186 (1988)). PCR was performed using TaKaRa LA Taq HS (Takara Bio Inc.) under reaction conditions specified in the instruction manual. The thus determined nucleotide sequence is shown in SEQ ID NO: 2 in the sequence listing. Also, the amino acid sequence encoded by the nucleotide sequence is shown in SEQ ID NO: 1 in the sequence listing.

Example 3

Construction of Recombinant Plasmid Containing TAT Gene

Based on the nucleotide sequence determined in Example 2, primer 3 (SEQ ID NO: 6 in the sequence listing) was synthesized by adding an Nde I site to an initiation codon of the TAT gene and primer 4 (SEQ ID NO: 7 in the sequence listing) was synthesized by adding an EcoR I site so that it immediately followed the termination codon of the TAT gene. PCR was performed using the chromosomal DNA of *Arthrobacter* sp. KNK04-25 obtained in Example 2 as a template and these primers. Thus, double-stranded DNA containing the Nde I site added to the initiation codon of the TAT gene and the EcoR I site added so that it immediately followed the termination codon was obtained. PCR was performed under reaction conditions specified in the instruction manual using a PrimeSTAR HS (Takara Bio Inc.). The DNA was digested with Nde I and EcoR I and then the digest was inserted between the Nde I recognition site and the EcoR I recognition site downstream of an lac promoter of plasmid pUCNT (WO94/03613), so that a pNTTAT recombinant vector was obtained.

Example 4

Preparation of Recombinant *Escherichia coli*

*E. coli* HB101 (Takara Bio Inc.) was transformed with the pNTTAT recombinant plasmid obtained in Example 3, and thus recombinant *E. coli* HB101 (pNTTAT) was obtained. As a comparative example, *E. coli* HB101 (Takara Bio Inc.) was transformed with the pUCNT plasmid, and thus recombinant *E. coli* HB101 (pUCNT) was obtained.

Example 5

Expression of TAT Gene Using Recombinant *Escherichia coli*

The transformant *E. coli* HB101 (pNTTAT) obtained in Example 4 and *E. coli* HB101 (pUCNT) as a comparative example were cultured in 2YT media (composition: 16 g/L triptone (Becton, Dickinson and Company), 10 g/L yeast extract (Becton, Dickinson and Company), 5 g/L NaCl (pH 7.0)) containing 200 µg/ml ampicillin. After cells were collected, each resultant was suspended in 100 mM phosphate buffer (pH 7.0). After disruption by ultrasonication, cell residues were removed by centrifugation, so that cell-free extracts were obtained.

The transaminase activity of the cell-free extracts was determined by the activity assay described in Example 1 using (S)-1-phenethylamine and 2-ketoglutaric acid as substrates. As a result, 5.0 U/ml activity was observed for the cell-free extract of *E. coli* HB101 (pNTTAT). No activity was observed for the cell-free extract of *E. coli* HB101 (pUCNT).

Example 6

Physico-Chemical Properties 1 of TAT

Activity of TAT for 1-benzyl-3-pyrrolidinone and optical purity of generated (S)-1-benzyl-3-aminopyrrolidine were examined using the cell-free extracts obtained in Example 5. (Method for Determination of Activity for 1-benzyl-3-pyrrolidinone and Method for Measurement of Optical Purity of Generated (S)-1-benzyl-3-aminopyrrolidine)

Activity to catalyze transamination by acting on optically active (S)-1-phenethylamine and 1-benzyl-3-pyrrolidinone, so as to generate acetophenone and (S)-1-benzyl-3-aminopyrrolidine was examined. Each reagent was added to each cell-free extract obtained in Example 5 so that the final concentrations were as specified in the following composition of the substrate solution. After 2 hours of reaction at 30° C., the reaction solution was analyzed by HPLC under the following conditions.

As a result, (S)-1-benzyl-3-aminopyrrolidine was generated with a 100% conversion rate and the optical purity was 100% e.e.

[Composition of Substrate Solution]

| | |
|---|---|
| 1-benzyl-3-pyrrolidinone | 57 mM |
| (S)-1-phenethylamine | 57 mM |
| Pyridoxal phosphate | 0.5 mM |
| Potassium phosphate buffer (pH 7.0) | 0.1 M |

[High Performance Liquid Chromatography Analysis Conditions]
<Quantitative Analysis>
Column: Finepak SIL C18-T (JASCO Corporation)
Eluent: distilled water 945 mL/acetonitrile 555 mL/$KH_2PO_4$ 7.5 g/SDS 2.16 g (adjusted with $H_3PO_4$ to pH 3.6)
Flow rate: 1 mL/minute
Detection: 254 nm
Column temperature: 40° C.
<Analysis of Optical Purity>
A reaction solution was treated with an appropriate amount of sodium carbonate, so that it became basic, derivatized with dinitrobenzoyl chloride, and then analyzed under the following conditions.
Column: Chiralpak IA (Daicel Corporation)
Eluent: hexane/ethanol/diethylamine/acetonitrile=800/200/1/5 (volume ratio)
Flow rate: 0.8 mL/minute
Detection: 254 nm
Column temperature: 30° C.

Example 7

Physico-Chemical Properties 2 of TAT

With the use of the cell-free extracts obtained in Example 5, the transamination activity of TAT was determined by the activity assay described in Example 1 using (S)-1-phenethylamine and 2-ketoglutaric acid as substrates.
(1) Optimum pH:
Transamination activity was determined in a manner similar to that described above with pH 4.0 to 10 and then the optimum pH of TAT was examined (buffers listed below were used in accordance with the pH employed for determination). As a result, transamination activity was the highest at pH 7. Transamination activity at pH 7.0 was designated as "100." pHs, at which transamination activity of "70 or more" was confirmed relative to activity of "100" at pH 7.0, were pH 7.0 and pH 8.0.
Buffer
pH 4.0 and pH 5.0: 0.1 M sodium acetate buffer
pH 6.0 and pH 7.0: 0.1 M potassium phosphate buffer
pH 8.0: 0.1 M tris-hydrochloric acid buffer
pH 9.0 and pH 10: 0.1 M sodium carbonate buffer (2) Optimum Temperature:

Transamination activity was determined in a manner similar to the above activity assay at temperatures (30° C., 40° C., 50° C., 60° C., and 70° C.). The optimum temperature of TAT was examined. As a result, transamination activity was the highest at 40° C. Transamination activity at 40° C. was designated as "100." Temperatures, at which transamination activity of "70 or more" was confirmed relative to activity of "100" at 40° C., were 30° C., 40° C., and 50° C.

(3) Thermal Stability:

The enzyme solutions were treated at temperatures (30° C., 40° C., 50° C., 60° C., and 70° C.) in a 0.5 mM pyridoxal phosphate and 0.1 M potassium phosphate buffer (pH 8.0) for 30 minutes. Then transamination activity was determined by the above activity assay to examine the thermal stability of TAT. Transamination activity before treatment was designated as "100." As a result, temperatures at which activity of "70 or more" was confirmed relative to activity of "100" before treatment were 30° C., 40° C., and 50° C.

Example 8

Physico-Chemical Properties 3 of TAT

The molecular weight of TAT was examined using the cell-free extracts obtained in Example 5.

Sodium dodecyl sulfate-polyacrylamide gel electrophoresis was performed using 10% polyacrylamide gel (ATTO Corporation). Perfect Protein Markers (Novagen) were used as standard proteins. Through comparison with the mobilities of the standard proteins, the molecular weight of TAT was calculated to be about 48 kDa.

Example 9

Physico-Chemical Properties 4 of TAT: Specificity to Amino group donor

The substrate specificity of TAT to amino group donors was examined using the cell-free extracts obtained in Example 5.

Each reagent was added to the enzyme solution (100 µL, each) so that the final concentrations were as specified in the following composition of the substrate solution. The volume of each reaction solution was adjusted to 400 µl with 0.1 M potassium phosphate buffer (pH 7.0). After 60 minutes of reaction at 30° C., 20 µL of 3N hydrochloric acid was added to stop the reaction. Next, 80 µL of a 0.2 M aqueous sodium carbonate solution and 200 µL of an acetone solution of 3.3 mg/mL Dabsyl chloride were each added to 20 µL of the thus obtained reaction solution, followed by 10 minutes of reaction at 70° C. Acetic acid (20 µL) was added to 50 µL of the reaction solution and then the solution was stirred. The resultant was analyzed by high performance liquid chromatography under the following conditions and thus the quantity of dabsylated glutamic acid was determined. In addition, the activity of an enzyme used in this assay was adjusted so that the amount of glutamic acid generated was 2.8 mM or less.

Table 1 shows the results. Specifically, Table 1 shows activity relative to activity confirmed when benzylamine was used as an amino group donor and designated as "100." As shown in Table 1, TAT exhibited activity for benzylamine, ±2-butylamine, and n-butylamine.

[Composition of Substrate Solution]

| Various amino compounds | 14 mM |
| --- | --- |
| 2-ketoglutaric acid | 14 mM |
| Pyridoxal phosphate | 0.5 mM |
| Potassium phosphate buffer (pH 7.0) | 0.1 M |

[High Performance Liquid Chromatography Analysis Conditions]

Column: Cosmosil 5C8-MS (NACALAI TESQUE, INC.)
Eluent: distilled water 2000 mL/acetonitrile 500 mL/methanol 500 ml/$KH_2PO_4$ 6.1 g/$H_3PO_4$ 2.5 g
Flow rate: 1 mL/minute
Detection: 254 nm
Column temperature: 30° C.

TABLE 1

| Amino group donor | Relative activity (%) |
| --- | --- |
| Benzylamine | 100 |
| ±2-butylamine | 7 |
| n-butylamine | 4 |

Example 10

Physico-Chemical Properties 5 of TAT: Specificity 2 to Amino Group Donor

With the use of the cell-free extracts obtained in Example 5, the reactivity of TAT to a typical substrate of co-amino acid transaminase was examined.

Each reagent was added to the enzyme solution (100 µL each) so that the final concentrations were as specified in the following composition of the substrate solution. The volume of each reaction solution was adjusted to 400 µl with 0.1 M potassium phosphate buffer (pH 7.0). After 60 minutes of reaction at 30° C., 20 µL of 3N hydrochloric acid was added to stop the reaction. Next, 80 µL of a 0.2 M aqueous sodium carbonate solution and 200 µL of an acetone solution of 3.3 mg/mL Dabsyl chloride were each added to 20 µL of the thus obtained reaction solution, followed by 10 minutes of reaction at 70° C. Acetic acid (20 µL) was added to 50 µL of the reaction solution and then the solution was stirred. The resultant was analyzed by high performance liquid chromatography under the following conditions and thus the quantity of dabsylated glutamic acid was determined. In addition, the activity of an enzyme used in this assay was adjusted so that the amount of glutamic acid generated was 2.8 mM or less.

Table 2 shows the results. Specifically, Table 2 shows activity relative to activity confirmed when (S)-1-phenethylamine was used as an amino group donor and designated as "100." As shown in Table 2, the polypeptide did not exhibit activity for β-alanine, 4-aminobutyric acid, 5-aminovaleric acid, 6-aminocaproic acid, ±2,4-diaminobutyric acid, L-ornithine, L-lysine, and putrescine.

[Composition of Substrate Solution]

| Various amino compounds | 14 mM |
| --- | --- |
| 2-ketoglutaric acid | 14 mM |
| Pyridoxal phosphate | 0.5 mM |
| Potassium phosphate buffer (pH 7.0) | 0.1 M |

[High Performance Liquid Chromatography Analysis Conditions]
Column: YMC-Pack Pro C18 RS (YMC)
Eluent: acetonitrile/45 mM acetate buffer (pH 4.1)=35/65 (volume ratio)
Flow rate: 0.9 mL/minute
Detection: 254 nm
Column temperature: 30° C.

TABLE 2

| Amino group donor | Relative activity (%) |
|---|---|
| (S)-α-phenethylamine | 100 |
| β-alanine | 0 |
| 4-aminobutyric acid | 0 |
| 5-aminovaleric acid | 0 |
| 6-aminocaproic acid | 0 |
| ±2,4-diaminobutyric acid·HCl | 0 |
| L-ornithine·HCl | 0 |
| L-lysine·HCl | 0 |
| Putrescine·2HCl | 0 |

Example 11

Physico-Chemical Properties 6 of TAT: Specificity 3 to Amino Group Donor

With the use of the cell-free extracts obtained in Example 5, the substrate specificity of TAT to an amino group donor was examined. Each reagent was added to enzyme solutions (200 µL each) so that the final concentrations were as specified in the following composition of the substrate solution. The volume of each reaction solution was adjusted to 400 µl with 0.1 M potassium phosphate buffer (pH 7.0). After 90 minutes of reaction at 30° C., 15 µL of 6N hydrochloric acid was added to stop the reaction. The thus obtained reaction solutions were analyzed by high performance liquid chromatography under the following conditions.

Table 3 shows the results. Specifically, Table 3 shows activity relative to activity confirmed when L-alanine was used as an amino group donor and designated as "100." As shown in Table 3, TAT exhibited higher activity for L-glutamic acid than that for L-alanine.

[Composition of Substrate Solution]

| 1-benzyl-3-pyrrolidinone | 29 mM |
|---|---|
| Various amino compounds | 290 mM |
| Pyridoxal phosphate | 0.5 mM |
| Potassium phosphate buffer (pH 7.0) | 0.1 M |

[High Performance Liquid Chromatography Quantitative Analysis Conditions]
<Quantitative Analysis>
Column: Finepak SIL C18-T (JASCO Corporation)
Eluent: distilled water 945 mL/acetonitrile 555 mL/KH$_2$PO$_4$ 7.5 g/SDS 2.16 g (adjusted with H$_3$PO$_4$ to pH 3.6)
Flow rate: 1 mL/minute
Detection: 254 nm
Column temperature: 40° C.
<Analysis of Optical Purity>
Each reaction solution was treated with an appropriate amount of sodium carbonate so that it became basic, derivatized with dinitrobenzoyl chloride, and then analyzed under the following conditions.

Column: Chiralcel IA (Daicel Corporation)
Eluent: hexane/ethanol/diethylamine/acetonitrile=800/200/1/5 (volume ratio)
Flow rate: 0.8 mL/minute
Detection: 254 nm
Column temperature: 30° C.

TABLE 3

| Amino group donor | Relative activity (%) |
|---|---|
| L-glutamic acid | 1650 |
| L-alanine | 100 |

Example 12

Physico-Chemical Properties 7 of TAT: Specificity to Amino Group Receptor

With the use of the cell-free extracts obtained in Example 5, the substrate specificity of TAT to an amino group receptor was examined.

Each reagent was added to the enzyme solution (100 µL each) so that the final concentrations were as specified in the following composition of the substrate solution. The volume of each reaction solution was adjusted to 400 µl with 0.1 M potassium phosphate buffer (pH 7.0). After 60 minutes of reaction at 30° C., 50 µL of 6N hydrochloric acid was added to stop the reaction. The thus obtained reaction solution was analyzed by high performance liquid chromatography under the following conditions and then the quantity of the thus generated acetophenone was determined.

Table 4 shows the results. Specifically, Table 4 shows activity relative to activity confirmed when 2-ketoglutaric acid was used as an amino group receptor and designated as "100". As shown in Table 4, the polypeptide exhibited high activity for 2-ketoglutaric acid and also exhibited activity for glyoxylic acid and pyruvic acid.

[Composition of Substrate Solution]

| Various ketone compounds | 14 mM |
|---|---|
| (S)-1-phenethylamine | 14 mM |
| Pyridoxal phosphate | 0.5 mM |
| Potassium phosphate buffer (pH 7.0) | 0.1 M |

[High Performance Liquid Chromatography Analysis Conditions]
Column: Cosmosil 5C8-MS (NACALAI TESQUE, INC.)
Eluent: distilled water 2000 mL/acetonitrile 500 mL/methanol 500 ml/KH$_2$PO$_4$ 6.1 g/H$_3$PO$_4$ 2.5 g
Flow rate: 1 mL/minute
Detection: 254 nm
Column temperature: 30° C.

TABLE 4

| Amino group receptor | Relative activity (%) |
|---|---|
| 2-ketoglutaric acid | 100 |
| Glyoxalic acid | 40 |
| Pyruvic acid | 10 |
| Phenylpyruvic acid | 8 |
| Oxalacetic acid | 4 |
| 2-ketobutyric acid | 5 |

TABLE 4-continued

| Amino group receptor | Relative activity (%) |
| --- | --- |
| 2-keto-n-valeric acid | 3 |
| Acetone | 0 |
| 2-butanone | 0 |
| 2-pentanone | 1 |
| 3-pentanone | 1 |
| 2-hexanone | 4 |
| 2-heptanone | 3 |
| 3-heptanone | 5 |
| Benzyl phenyl ketone | 0 |
| Butylaldehyde | 6 |
| Benzaldehyde | 70 |
| 7-methoxy-2-tetralone | 0 |
| α-cyanoacetophenone | 0 |
| 2-acetylpyridine | 60 |
| 1-benzyl-3-pyrrolidinone | 20 |
| 3-oxopentanenitrile | 0 |
| Methyl 3-oxovalerate | 4 |
| Methyl 3-oxohexanoate | 4 |
| Ethyl acetoacetate | 2 |
| 4-hydroxy butane-2-one | 0 |
| Quinuclidinone | 0 |
| 1-tetralone | 1 |
| 2-tetralone | 1 |

Example 13

Cloning of *Lactobacillus paracasei* sub sp. *paracasei* JCM1181-Derived D-hydroxyisocaproate Dehydrogenase Gene (RLC)

The gene of D-hydroxyisocaproate dehydrogenase (hereinafter, abbreviated as "RLC") that is one of α-keto acid reductase was cloned from *Lactobacillus paracasei* sub sp. *paracasei*) JCM1181 by the following method. Persons skilled in the art can obtain the *Lactobacillus paracasei* sub sp. *Paracasei* JCM1181 strain from RIKEN BioResource Center (2-1, Hirosawa, Wako, Saitama, Japan, 351-0198). The RLC is an example of the "α-keto acid reductase (β)" of the present invention.
(Preparation of PCR Primer)

Based on the gene sequence information (Genebank M26929) of known D-hydroxyisocaproate dehydrogenase registered in the gene databank, primer 5 (SEQ ID NO: 8 in the sequence listing) was synthesized by adding an Nde I site to the initiation codon of the RLC gene and primer 6 (SEQ ID NO: 9 in the sequence listing) was synthesized by adding a Kpn I site so that it immediately followed the termination codon of the RLC gene. Also, primer 7 (SEQ ID NO: 10 in the sequence listing) and primer 8 (SEQ ID NO: 11 in the sequence listing) were synthesized by substituting the 165$^{th}$ A with G in order to disrupt the Nde I site existing within the RLC gene.
(Amplification of RLC Gene by PCR)

Chromosomal DNA was extracted from the culture solution of *Lactobacillus paracasei* sub sp. *paracasei*) JCM1181 according to the method of Ausubel et al. (as described in Current Protocols in Molecular Biology, 1987). PCR was performed using the thus obtained chromosomal DNA as a template and the primers 5 and 7 synthesized above. As a result, an about 200-bp DNA fragment (thought to be a portion of the gene) was obtained. PCR was further performed using the primers 6 and 8. As a result, an about 1800-bp DNA fragment (thought to be a portion of the gene) was obtained. Subsequently, the 2 types of the above PCR fragments were purified according to the instruction manual of a QIAquick PCR purification Kit (QIAGEN) and then mixed. PCR was then performed. As a result, a restriction enzyme site was added to the full-length gene and then an about 2000-bp DNA fragment (thought to have the disrupted Nde I site) was obtained. PCR was performed using TaKaRa PrimeSTAR (Takara Bio Inc.) as DNA polymerase under reaction conditions specified in the instruction manual.

The nucleotide sequence of the DNA fragment was determined using an ABI PRISM Dye Terminator Cycle Sequencing Ready Reaction Kit (Applied Biosystems) and an ABI 3100 DNA Sequencer (Applied Biosystems). The nucleotide sequence is shown in SEQ ID NO: 12 in the sequence listing.

Example 14

Construction of Recombinant Plasmid Containing RLC Gene

PCR was performed using the PCR fragment obtained in Example 13 as a template and the primer 5 (SEQ ID NO: 8 in the sequence listing) and the primer 6 (SEQ ID NO: 9 in the sequence listing). Double-stranded DNA was obtained by adding an Nde I site to the initiation codon of the RLC gene, adding a Kpn I site so that it immediately followed the termination codon, and disrupting the Nde I site within the RLC gene. PCR was performed using PrimeSTAR (Takara Bio Inc.) under reaction conditions specified in the instruction manual. The DNA was digested with Nde I and Kpn I, and then the digest was inserted between the Nde I recognition site and the Kpn I recognition site downstream of the lac promoter of plasmid pUCNT (WO94/03613), so that a pNTLC recombinant vector was obtained.

Example 15

Preparation of Recombinant *Escherichia coli* Expressing RLC

*E. coli* HB101 (Takara Bio Inc.) was transformed with the pNTLC recombinant plasmid constructed in Example 14, so that recombinant *E. coli* HB101 (pNTLC) was obtained.

The above transformant *E. coli* HB101 (pNTLC) was cultured in 2YT medium (composition: 16 g/L tryptone (Becton, Dickinson and Company), 10 g/L yeast extract (Becton, Dickinson and Company), 5 g/L NaCl (pH 7.0)) containing 200 μg/ml ampicillin. After cells were collected, the resultant was suspended in 100 mM phosphate buffer (pH 7.0). After disruption by ultrasonication, cell residues were removed by centrifugation, so that a cell-free extract was obtained.

The cell-free extract was added to a solution prepared by adding 2-ketoglutaric acid (to have a final concentration of 20 mM) and coenzyme NADH (to have a final concentration of 0.25 mM) to 100 mM phosphate buffer (pH 6.5), followed by 1 minute of reaction at 30° C. Activity was found by calculation based on the rate of decrease in absorbance at a wavelength of 340 nm of the reaction solution. Under the reaction conditions, activity to oxidize 1 μmol of NADH to NAD+ per minute was defined as 1 U.

As a result, 30 U/ml activity was observed for the cell-free extract of *E. coli* HB101 (pNTLC).

Example 16

Production of Optically Active 1-benzyl-3-aminopyrrolidine by Production Method I Activity to catalyze transamination which generates (S)-1-benzyl-3-aminopyrrolidine using L-glutamic acid and 1-benzyl-3-pyrrolidinone as substrates was examined.

Reaction (1)

A TAT polypeptide cell-free extract obtained in Example 5 was prepared to have a final concentration of 5 U/mL TAT. Each reagent was added to the enzyme solution so that the final concentrations were as specified in the following composition 1 of the substrate solution. After 2 hours of reaction at 30° C., the reaction solution was analyzed by HPLC under the following conditions.

Reaction (2)

The TAT polypeptide cell-free extract obtained in Example 5, the RLC enzyme cell-free extract obtained in Example 15, and commercially available glucose dehydrogenase (Amano Enzyme inc.) were mixed so that the final concentration of TAT was 5 U/mL, the same of RLC was 2 U/mL, and the same of the commercially available glucose dehydrogenase was 8 U/mL. Each reagent was added to the enzyme solution so that the final concentrations were as specified in the following composition 2 of the substrate solution. After 2 hours of reaction at 30° C., the reaction solution was analyzed by HPLC under the following conditions.

Table 5 shows the relative production amount when the amount of (S)-1-benzyl-3-aminopyrrolidine generated by the reaction (1) was designated as 100. As shown in Table 5, the amount generated in the case of the reaction (2) (the RLC enzyme and glutamate dehydrogenase had been conjugated with the TAT polypeptide) was twice as high as that in the case of the reaction (1).

[Composition 1 of Substrate Solution]

| 1-benzyl-3-pyrrolidinone | 57 mM |
| Sodium L-glutamate | 171 mM |
| Pyridoxal phosphate | 0.5 mM |
| Potassium phosphate buffer (pH 7.0) | 0.1 M |

[Composition 2 of Substrate Solution]

| 1-benzyl-3-pyrrolidinone | 57 mM |
| Sodium L-glutamate | 171 mM |
| D-glucose | 57 mM |
| NADH | 0.6 mM |
| Pyridoxal phosphate | 0.5 mM |
| Potassium phosphate buffer (pH 7.0) | 0.1 M |

[High Performance Liquid Chromatography Analysis Conditions]

<Quantitative Analysis>

Column: Finepak SIL C18-T (JASCO Corporation)

Eluent: distilled water 945 mL/acetonitrile 555 mL/$KH_2PO_4$ 7.5 g/SDS 2.16 g (adjusted with $H_3PO_4$ to pH 3.6)

Flow rate: 1 mL/minute

Detection: 254 nm

Column temperature: 40° C.

TABLE 5

| Reaction | Relative amount of compound generated (%) |
|---|---|
| Reaction (1) | 100 |
| Reaction (2) | 230 |

Example 17

Production 2 of Optically Active 1-benzyl-3-aminopyrrolidine by Production Method I E. coli HB101 (pNTTAT) strain obtained in Example 4 was cultured in 2×YT medium (tryptone 1.6%, yeast extract 1.0%, NaCl 0.5%, pH 7.0) containing 200 μg/ml ampicillin, and then cells were collected. Furthermore, E. coli HB101 (pNTLC) strain obtained in Example 15 was cultured in 2×YT medium (tryptone 1.6%, yeast extract 1.0%, NaCl 0.5%, pH 7.0) containing 200 μg/ml ampicillin, and then cells were collected.

The above cell suspension and commercially available glucose dehydrogenase (Amano Enzyme inc.) were mixed in a flask containing 150 mg of 1-benzyl-3-pyrrolidinone as a substrate, 1.6 g of sodium L-glutamate, 150 mg of D-glucose, and 6 mg of NADH, so that the final concentration of TAT was 5 U/mL, the same of RLC was 2 U/mL, and the same of commercially available glucose dehydrogenase was 8 U/mL. Two (2) mg of pyridoxal phosphate, 1.5 mL of 1 M potassium phosphate buffer (pH 7.5), and deionized water were added, so that the total volume was 30 mL. The solution was adjusted with sodium hydroxide to have pH 7.5 at 30° C. and then reaction was performed for 24 hours while stirring. After the completion of the reaction, the reaction solution was analyzed by HPLC under the following conditions.

As a result, 1-benzyl-3-aminopyrrolidine was generated with a conversion rate of 36%. The configuration thereof was (S)-configuration and the optical purity was 99% e.e.

[High Performance Liquid Chromatography Quantitative Analysis Conditions]

<Quantitative Analysis>

Column: Finepak SIL C18-T (JASCO Corporation)

Eluent: distilled water 945 mL/acetonitrile 555 mL/$KH_2PO_4$ 7.5 g/SDS 2.16 g (adjusted with $H_3PO_4$ to pH 3.6)

Flow rate: 1 mL/minute

Detection: 254 nm

Column temperature: 40° C.

<Analysis of Optical Purity>

The reaction solution was treated with an appropriate amount of sodium carbonate so that it became basic, derivatized with dinitrobenzoyl chloride, and then analyzed under the following conditions.

Column: Chiralcel IA (Daicel Corporation)

Eluent: hexane/ethanol/diethylamine/acetonitrile=800/200/1/5 (volume ratio)

Flow rate: 0.8 mL/minute

Detection: 254 nm

Column temperature: 30° C.

Example 18

Production 3 of Optically Active 1-benzyl-3-aminopyrrolidine by Production Method I E. coli HB101(pNTTAT) obtained in Example 4 was cultured in 2×YT medium (tryptone 1.6%, yeast extract 1.0%, NaCl 0.5%, pH 7.0) containing 200 μg/ml ampicillin, and then cells were collected.

The above cell suspension, commercially available glutamate dehydrogenase (mpbio), and commercially available glucose dehydrogenase (Amano Enzyme inc.) were mixed in a flask containing 150 mg of 1-benzyl-3-pyrrolidinone as a substrate, 1.6 g of sodium L-glutamate, 110 mg of diammonium phosphate, 150 mg of D-glucose, and 6 mg of NADH, so that the final concentration of TAT was 5 U/mL, the same of commercially available glutamate dehydrogenase (mpbio) was 2 U/mL, and the same of commercially available glucose dehydrogenase (Amano Enzyme inc.) was 3 U/mL. Two (2) mg of pyridoxal phosphate, 1.5 mL of 1 M potassium phosphate buffer (pH 7.5), and deionized water were added, so that the total volume was 30 mL. The solution was adjusted with sodium hydroxide to have pH 7.5 at 30° C. and then reaction was performed for 24 hours while stirring. After the completion of the reaction, the reaction solution was analyzed by HPLC under the following conditions.

As a result, 1-benzyl-3-aminopyrrolidine was generated with a conversion rate of 35%. The configuration was (S) configuration and the optical purity was 99% e.e.

[High Performance Liquid Chromatography Quantitative Analysis Conditions]
<Quantitative Analysis>
Column: Finepak SIL C18-T (JASCO Corporation)
Eluent: distilled water 945 mL/acetonitrile 555 mL/$KH_2PO_4$ 7.5 g/SDS 2.16 g (adjusted with $H_3PO_4$ to pH 3.6)
Flow rate: 1 mL/minute
Detection: 254 nm
Column temperature: 40° C.
<Analysis of Optical Purity>
The reaction solution was treated with an appropriate amount of sodium carbonate so that it became basic, derivatized with dinitrobenzoyl chloride, and then analyzed under the following conditions.
Column: Chiralcel IA (Daicel Corporation)
Eluent: hexane/ethanol/diethylamine/acetonitrile=800/200/1/5 (volume ratio)
Flow rate: 0.8 mL/minute
Detection: 254 nm
Column temperature: 30° C.

All publications, patents, and patent applications cited herein are incorporated herein by reference in their entirety.

---

The invention claimed is:

1. A DNA consisting of a nucleotide sequence encoding a polypeptide selected from the group consisting of:

(a) a polypeptide consisting of an amino acid sequence that is identical to the amino acid sequence of SEQ ID NO: 1 except for a deletion, a substitution, an insertion, and/or an addition of 1 to 20 amino acids in SEQ ID NO: 1, wherein said polypeptide catalyzes the transamination of 1-benzyl-3-pyrrolidinone in the presence of an amino group donor to generate (S)-1-benzyl-3-aminopyrrolidine with optical purity of 93% enantiomeric excess or more;

(b) a polypeptide consisting of an amino acid sequence that is identical to the amino acid sequence of SEQ ID NO: 1 except for a deletion, a substitution, an insertion, and/or an addition of 1 to 20 amino acids in sequence of SEQ ID NO: 1, and wherein said polypeptide catalyzes the transamination of 1-benzyl-3-pyrrolidinone in the presence of an amino group donor to generate ((S)-1-benzyl -3-aminopyrrolidine with optical purity of 93% enantiomeric excess or more, wherein said polypeptide exhibits higher activity for 2-ketoglutaric acid than that for pyruvic acid as an amino group receptor; wherein said polypeptide exhibits activity for (S)-1-phenethylamine as an amino donor, wherein said polypeptide exhibits higher activity for L-glutamic acid than that for L-alanine as an amino donor, and wherein said polypeptide does not substantially exhibit activity for β-alanine or 4-aminobutyric acid as an amino group donor;

(c) a polypeptide consisting of an amino acid sequence that is identical to the amino acid sequence of SEQ ID NO: 1 except for a deletion, a substitution, an insertion, and/or an addition of 1 to 20 amino acids in SEQ ID NO: 1, wherein said polypeptide has an optimum pH ranging from 7.0 to 8.0, wherein said polypeptide has an optimum temperature ranging from 30° C. to 50° C., wherein said polypeptide retains a residual activity equivalent to 70% or more of the activity before treatment when treated at 30° C. to 50° C. for 30 minutes, wherein said polypeptide has a molecular weight of about 48 kDa as measured by sodium dodecyl sulfate-polyacrylamide gel electrophoresis, and wherein said polypeptide catalyzes the transamination of 1-benzyl-3-pyrrolidinone in the presence of an amino group donor to generate (S)-1-benzyl-3-aminopyrrolidine with optical purity of 93% enantiomeric excess or more.

2. A vector comprising a DNA consisting of a nucleotide sequence encoding a polypeptide selected from the group consisting of:
(a) a polypeptide consisting of the amino acid sequence of SEQ ID NO: 1;
(b) a polypeptide consisting of an amino acid sequence is identical to the amino acid sequence of SEQ ID NO: 1 except for a deletion, a substitution, an insertion, and/or an addition of 1 to 20 amino acids in SEQ ID NO: 1, wherein said polypeptide catalyzes the transamination of 1-benzyl-3-pyrrolidinone in the presence of an amino group donor to generate (S)-1-benzyl-3-aminopyrrolidine with optical purity of 93% enantiomeric excess or more;
(c) a polypeptide consisting of an amino acid sequence that is identical to the amino acid sequence of SEQ ID NO: 1 except for a deletion, a substitution, an insertion, and/or an addition of 1 to 20 amino acids in SEQ ID NO: 1, wherein said polypeptide catalyzes the transamination of 1-benzyl-3-pyrrolidinone in the presence of an amino group donor to generate (S)-1-benzyl-3-aminopyrrolidine with optical purity of 93% enantiomeric excess or more, wherein said polypeptide exhibits higher activity for 2-ketoglutaric acid than that for pyruvic acid as an amino group receptor; wherein said polypeptide exhibits activity for S)-1-phenethylamine as an amino donor, wherein said polypeptide exhibits higher activity for L-glutamic acid than that for L-alanine as an amino donor, and wherein said polypeptide does not substantially exhibit activity for β-alanine or 4-aminobutyric acid as an amino group donor;
(d) a polypeptide consisting of an amino acid sequence that is identical to the amino acid sequence of SEQ ID NO: 1 except for a deletion, a substitution, an insertion, and/or an addition of 1 to 20 amino acids in SEQ ID NO: 1, wherein said polypeptide has an optimum pH ranging from 7.0 to 8.0, wherein said polypeptide has an optimum temperature ranging from 30° C. to 50° C., wherein said polypeptide retains a residual activity equivalent to 70% or more of the activity before treatment when treated at 30° C. to 50° C. for 30 minutes, wherein said polypeptide has a molecular weight of about 48 kDa as measured by sodium dodecyl sulfate-polyacrylamide gel electrophoresis, and wherein said polypeptide catalyzes the transamination of 1-benzyl-3-pyrrolidinone in the presence of an amino group donor to generate (S)-1-benzyl-3-aminopyrrolidine with optical purity of 93% enantiomeric excess or more;
(e) a polypeptide consisting of an amino acid sequence which is at least 95% sequence identical to SEQ ID NO: 1, and having activity to act on 1-benzyl-3-pyrrolidinone in the presence of an amino group donor to generate (S)-1-benzyl-3-aminopyrrolidine with optical purity of 93% enantiomeric excess or more;
(f) a polypeptide consisting of an amino acid sequence which is at least 95% sequence identical to SEQ ID NO: 1, wherein said polypeptide catalyzes the transamination of 1-benzyl-3-pyrrolidinone in the presence of an amino group donor to generate (S)-1-phenethylamine with optical purity of 93% enantiomeric excess or more, wherein said polypeptide exhibits higher activity for 2-ketoglutaric acid than that for pyruvic acid as an amino group receptor; wherein said polypeptide exhibits activity for (S)-1-phenethylamine as an amino donor, wherein said polypeptide exhibits higher activity for L-glutamic acid than that for L-alanine as an amino donor, and wherein said polypeptide does not substantially exhibit activity for β-alanine or 4-aminobutyric acid as an amino group donor; and
(g) a polypeptide consisting of an amino acid sequence which is at least 95% sequence identical to SEQ ID NO: 1, wherein said polypeptide has an optimum pH ranging from 7.0 to 8.0, wherein said polypeptide has an optimum temperature ranging from 30° C. to 50° C., wherein said polypeptide retains residual activity equivalent to 70% or more of the activity before treatment when treated at 30° C. to 50° C. for 30 minutes, wherein said polypeptide has a molecular weight of about 48 kDa as measured by sodium dodecyl sulfate-polyacrylamide gel electrophoresis, and wherein said polypeptide catalyzes the transamination of 1-benzyl-3-pyrrolidinone in the presence of an amino group donor to generate (S)-1-benzyl-3-aminopyrrolidine with optical purity of 93% enantiomeric excess or more.

3. A transformant which is obtained by transforming a host cell with the vector of claim 2.

* * * * *

SEQUENCE LISTING

```
<160> NUMBER OF SEQ ID NOS: 12

<210> SEQ ID NO 1
<211> LENGTH: 448
<212> TYPE: PRT
<213> ORGANISM: Arthrobacter sp.

<400> SEQUENCE: 1

Met Ser Ala Ile Thr Leu Glu Ser Ser Leu Ala Thr Phe Thr Arg Arg
1               5                   10                  15

Phe Asp Val Ser Ala Lys Leu Thr Glu Leu Gly Lys Glu Val Val Pro
                20                  25                  30

Gly Gly Tyr Ser Arg Asn Ser Phe Asn Phe Gly Pro His Ala Ile Tyr
            35                  40                  45

Val Glu Ser Gly Asp Gly Ala Tyr Ile Ser Thr Val Glu Gly His Arg
    50                  55                  60

Leu Leu Asp Leu Asn Asn Asn Phe Thr Val Asn Val Leu Gly His Asn
65                  70                  75                  80

His Pro Ser Val Gln Arg Thr Leu Arg Gly Ser Ile Glu Thr Gly Val
                85                  90                  95

Ser Phe Gly Asn Pro Val Ala Leu Glu Thr Glu Leu Ala Gln Leu Leu
            100                 105                 110

Val Glu Arg Ile Pro Ser Ile Glu Arg Val Gln Phe Ser Cys Ser Ala
        115                 120                 125

Ser Glu Ser Cys Met Ser Ala Val Arg Val Ala Arg Ala Phe Thr Gly
    130                 135                 140

Arg Thr Lys Ile Ala Lys Phe Glu Gly Gly Tyr His Gly Phe Thr Asp
145                 150                 155                 160

Pro Leu Gln Val Ser Trp His Pro Asp His Asp Gly Asp Cys Gly Pro
                165                 170                 175

Asp Asp Ala Pro Lys Ala Ile Pro Asp Ser Gly Gly Ile Pro Ala Glu
            180                 185                 190

Asp Val Ala Asn Val Val Leu Thr Gln Asn Asp Gly Glu Gly Thr
        195                 200                 205

Glu Arg Ile Leu Arg Ala His Ala Ser Glu Ile Ala Cys Val Ile Val
    210                 215                 220
```

```
Glu Leu Glu Ser Ala Ser Gly Gly Leu Val Thr Leu Glu Gln Asp Tyr
225                 230                 235                 240

Val Glu Ser Leu Arg Glu Leu Thr Ser Glu Leu Gly Ile Val Leu Ile
            245                 250                 255

Phe Asp Glu Thr Val Thr Leu Arg Ala Gly Tyr Gln Gly Met Gln Gly
        260                 265                 270

Asp Tyr Gly Val Ala Pro Asp Leu Thr Val Met Gly Lys Ile Ile Gly
    275                 280                 285

Gly Gly Phe Pro Leu Gly Ala Val Gly Gly Ser Ala Glu Ile Met Ser
290                 295                 300

Val Leu Glu Ser Gly Leu Val Ser Ile Ser Gly Thr His His Gly His
305                 310                 315                 320

Lys Ile Ala Leu Ala Ala Gly Ile Ser Thr Met Arg Glu Leu Thr Gln
            325                 330                 335

Gly Ala Phe Asp Arg Leu Asn Gly Met Ala Thr Arg Val Met Glu Glu
        340                 345                 350

Leu Asn Asp Trp Ser Ser Gln Arg Gly Ser Ser Phe Ala Val Tyr Gly
    355                 360                 365

Lys Gly Ile Ser His Leu Ala Tyr Gly Phe Met Arg Glu Pro Gly Leu
370                 375                 380

Ser Ile Arg Thr His Arg Asp Tyr Trp Arg Asn Phe Asp Gly Thr Gly
385                 390                 395                 400

Thr Gln Ile Cys Ser Leu Glu Leu Ala Asn Arg Gly Phe Phe Pro Val
            405                 410                 415

Ala Arg Gly Asp Phe Ser Leu Ser Leu Pro Met Ser Asp Asp Asp Ile
        420                 425                 430

Thr Ala Phe Val Glu Thr Thr Lys Glu Ile Val Thr Gly Ile Glu Ser
    435                 440                 445

<210> SEQ ID NO 2
<211> LENGTH: 1347
<212> TYPE: DNA
<213> ORGANISM: Arthrobacter sp.

<400> SEQUENCE: 2
atgagcgcca ttaccctcga atcttccctc gcgactttca cacgtcgttt tgatgtatcg      60
gcgaagctga ctgagcttgg gaaggaagtt gtccccggcg gctacagccg caactccttc     120
aatttcggcc gcacgcgat ctatgtcgag agtggagatg gtgcttacat ttctacggtc     180
gaagggcatc ggctcctgga tctgaacaat aacttcacag tcaatgtgct aggacacaac     240
catccttctg tgcagagaac cttgcgtggg tccatcgaaa ccggggtttc gtttggtaac     300
cccgtggctc tcgagacgga actagcgcag ctgcttgtcg agcggattcc ttccattgaa     360
cgcgtgcaat tctcctgctc cgcatctgag tcctgtatgt ctgcggtacg tgtggcgcgt     420
gccttcacgg gccgcacgaa gatcgcgaag ttcgaaggcg ataccacgg ctttactgat     480 ccgcttcagg tgtcttggca ccccgaccac gatggagact gcggtcccga cgacgcgcca     540
aaggccatcc cggacagtgg aggcatccct gcggaggacg tagctaacgt ggtggttcta     600
acccaaaacg atggcgaggg gacggagcga atcctgcgag ctcatgcaag tgagatcgcc     660
tgcgttatcg tcgagctcga aagtgcttcc ggcggccttg taacgctaga gcaggactat     720
gtcgagagcc ttcgtgaact aacctcggag ttggggattg tcctgatctt cgatgagacc     780
gtaacccttc gtgccggcta tcaagggatg caggggggact acggggtggc acctgacctc     840
```

```
acagtgatgg gcaaaatcat cggtggaggc ttcccactcg gtgcagtagg cggctctgcc      900
gagatcatga gcgtcctgga gtcagggctt gtctccatct ccggcaccca ccacggtcat      960
aagatcgcct tggccgccgg tatttccacg atgagggagc tcactcaagg cgctttcgac     1020
cggctgaatg gaatggccac gcgggtgatg gaggagctaa acgactggag cagccagcgg     1080
ggcagcagct tcgccgtgta cggcaagggc atctcccatc tcgcttatgg attcatgcgt     1140
gaacctggct tgagcattcg gactcatcgc gactactggc ggaacttcga cggtaccgga     1200
acgcagattt gttcgctgga acttgctaat cgaggttttt tcccggtcgc tcgaggtgac     1260
ttctcgttgt cgttgccaat gagcgacgac gacatcacgg cctttgtcga aaccaccaag     1320
gagattgtca ccggcatcga aagctga                                         1347
```

<210> SEQ ID NO 3
<211> LENGTH: 19
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (2)..(2)
<223> OTHER INFORMATION: n represents a, t, g or c
<220> FEATURE:
<221> NAME/KEY: misc_feature
<222> LOCATION: (11)..(11)
<223> OTHER INFORMATION: n represents a, t, g or c
<220> FEATURE:
<221> NAME/KEY: misc_feature
<222> LOCATION: (14)..(14)
<223> OTHER INFORMATION: n represents a, t, g or c
<220> FEATURE:
<221> NAME/KEY: misc_feature
<222> LOCATION: (17)..(17)
<223> OTHER INFORMATION: n represents a, t, g or c

<400> SEQUENCE: 3
gnttygaygt ntcngcnaa                                                    19

<210> SEQ ID NO 4
<211> LENGTH: 23
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(3)
<223> OTHER INFORMATION: n represents a, t, g or c
<220> FEATURE:
<221> NAME/KEY: misc_feature
<222> LOCATION: (12)..(12)
<223> OTHER INFORMATION: n represents a, t, g or c
<220> FEATURE:
<221> NAME/KEY: misc_feature
<222> LOCATION: (15)..(15)
<223> OTHER INFORMATION: n represents a, t, g or c

<400> SEQUENCE: 4
aanccrtgrt anccnccytc raa                                               23

<210> SEQ ID NO 5
<211> LENGTH: 385
<212> TYPE: DNA
<213> ORGANISM: Arthrobacter sp.

<400> SEQUENCE: 5

| | | | | | | |
|---|---|---|---|---|---|---|
| gctgactgag | cttgggaagg | aagttgtccc | cggcggctac | agccgcaact | ccttcaattt | 60 |
| cggcccgcac | gcgatctatg | tcgagagtgg | agatggtgct | tacatttcta | cggtcgaagg | 120 |
| gcatcggctc | ctggatctga | acaataactt | cacagtcaat | gtgctaggac | acaaccatcc | 180 |
| ttctgtgcag | agaaccttgc | gtgggtccat | cgaaaccggg | gtttcgtttg | gtaacccgt | 240 |
| ggctctcgag | acggaactag | cgcagctgct | tgtcgagcgg | attccttcca | ttgaacgcgt | 300 |
| gcaattctcc | tgctccgcat | ctgagtcctg | tatgtctgcg | gtacgtgtgg | cgcgtgcctt | 360 |
| cacgggccgc | acgaagatcg | cgaag | | | | 385 |

<210> SEQ ID NO 6
<211> LENGTH: 30
<212> TYPE: DNA
<213> ORGANISM: Artificial
<220> FEATURE:
<223> OTHER INFORMATION: primer

<400> SEQUENCE: 6
ggaattccat atgagcgcca ttaccctcga          30

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
ccggaattct cagctttcga tgccggtga           29

<210> SEQ ID NO 8
<211> LENGTH: 45
<212> TYPE: DNA
<213> ORGANISM: Artificial
<220> FEATURE:
<223> OTHER INFORMATION: primer

<400> SEQUENCE: 8
aagtttaaca tatgaagatt attgcttacg gtgctcgcgt tgacg          45

<210> SEQ ID NO 9
<211> LENGTH: 45
<212> TYPE: DNA
<213> ORGANISM: Artificial
<220> FEATURE:
<223> OTHER INFORMATION: primer

<400> SEQUENCE: 9
tataggtacc ttactacttt gctggaccag taacttccgt gctgg          45

<210> SEQ ID NO 10
<211> LENGTH: 45
<212> TYPE: DNA
<213> ORGANISM: Artificial
<220> FEATURE:
<223> OTHER INFORMATION: primer

<400> SEQUENCE: 10
gcgtgcattt tttcaaaaac gccggctgca tacggcgttg tctgc          45

```
<210> SEQ ID NO 11
<211> LENGTH: 45
<212> TYPE: DNA
<213> ORGANISM: Artificial
<220> FEATURE:
<223> OTHER INFORMATION: primer

<400> SEQUENCE: 11
gcagacaacg ccgtatgcag ccggcgtttt tgaaaaaatg cacgc              45

<210> SEQ ID NO 12
<211> LENGTH: 1002
<212> TYPE: DNA
<213> ORGANISM: Lactobacillus paracasei subsp. paracasei

<400> SEQUENCE: 12
atgaagatta ttgcttacgg tgctcgcgtt gacgagattc aatatttcaa gcaatgggcc    60
aaggatacag gcaacacact tgaataccat acagaatttc tcgatgaaaa caccgttgaa   120
tgggctaaag ggtttgatgg catcaattca ttgcagacaa cgccgtatgc agccggcgtt   180
tttgaaaaaa tgcacgcgta tggtatcaag ttcttgacga ttcggaatgt gggtacggat   240
aacattgata tgactgccat gaagcaatac ggcattcgtt tgagcaatgt accggcttat   300
tcgccagcag cgattgctga atttgctttg accgatactt tgtacttgct acgtaatatg   360
ggtaaagtac aggcgcaact acaggcgggc gattatgaaa aagcgggcac cttcatcggt   420
aaggaactcg gtcagcaaac cgttggcgtg atgggcaccg gtcatattgg acaggttgct   480
atcaaactgt tcaaaggctt tggcgccaaa gtgattgctt acgatcctta tccaatgaag   540
ggcgatcacc cagattttga ctatgtcagc cttgaagacc tctttaagca aagtgatgtc   600
attgatcttc atgttcctgg gattgaacaa aatacccaca ttatcaatga agcggcattt   660
aatttgatga aaccgggtgc gattgtgatc aacacggctc ggccaaatct gattgacacg   720
caagccatgc tcagcaatct taagtctggc aagttggccg gtgtcgggat tgacacctat   780
gaatacgaaa ccgaggactt gttgaatctc gccaagcacg gcagcttcaa ggatccgttg   840
tgggatgagc tgttggggat gccaaatgtt gtcctcagcc cgcacattgc ctactacacc   900
gagacggctg tgcataatat ggtttacttc tcactacaac atctcgttga tttcttgacc   960
aaaggcgaaa ccagcacgga agttactggt ccagcaaagt ag                    1002
```